United States Patent [19]

Tsien et al.

[11] Patent Number: 5,141,627

[45] Date of Patent: Aug. 25, 1992

[54] CHELATORS WHOSE AFFINITY FOR CALCIUM ION IS INCREASED BY ILLUMINATION

[75] Inventors: Roger Y. Tsien, La Jolla; Stephen R. Adams, San Diego, both of Calif.

[73] Assignee: The Regents of the University of California, Oakland, Calif.

[21] Appl. No.: 412,852

[22] Filed: Sep. 25, 1989

[51] Int. Cl.⁵ .................... C07C 245/08; C07C 45/00
[52] U.S. Cl. .................... 204/157.88; 204/157.93; 534/564
[58] Field of Search .................... 534/564; 204/157.88, 204/157.93

[56] References Cited

U.S. PATENT DOCUMENTS

| | | | |
|---|---|---|---|
| 4,603,209 | 7/1986 | Tsien | 548/236 |
| 4,689,432 | 8/1987 | Tsien | 562/435 |
| 4,806,604 | 8/1989 | Tsien | 549/439 |

OTHER PUBLICATIONS

I. P. Mulligan & C. C. Ashley, "Rapid Relaxation of Single Frog Skeletal Muscle Fibres Following Laser Flash Photolysis of the Caged Calcium Chelator, Diazo-2", Federation of European Biochemical Societies, 1989, vol. 255, p. 196.

S. R. Adams, J. P. Y. Kao & R. Y. Tsien, "Biologically Useful Chelators That Take Up $Ca^{2+}$ Upon Illumination,", Journal of the American Chemical Society, 1989, vol. 111, pp. 7957-7968.

S. R. Adams, et al., "Biologically Useful Chelators That Release $Ca^{2+}$ Upon Illumination," Journal of the American Chemical Society, 1988, vol. 110, pp. 3212-3220.

Grzegorz Grynkiewicz, et al., "A New Generation of $Ca^{2+}$ Indicators with Greatly Improved Fluorescence Properties," The Journal of Biological Chemistry, 1985, vol. 260, pp. 3440-3450.

James A. McCray, "Properties and Uses of Photoreactive Caged Compounds," Annu. Rev. Biophys. Biophys. Chem., 1989, vol. 18, pp. 239-270.

Alison M. Gurney & Henry A. Lester, "Light-Flash Physiology With Synthetic Photosensitive Compounds," Physiological Reviews 1987, vol. 67, pp. 583-617.

Akwasi Minta, et al., "Fluorescent Indicators for Cytosolic Calcium Based on Rhodamine and Fluorescein Chromophores," The Journal of Biological Chemistry, 1989, vol. 264, pp. 8171-8178.

Primary Examiner—John F. Niebling
Assistant Examiner—Steven P. Marquis
Attorney, Agent, or Firm—Phillips, Moore, Lempio & Finley

[57] ABSTRACT

The present invention relates to a group of organic chelators whose affinity for calcium ion in solution is increased by electromagnetic radiation. Specifically, the chelators are related to BAPTA and utilize the addition of an electron-withdrawing group (e.g., diazocarbonyl) to a ring of BAPTA, para to the amino group. Photochemical rearrangement of the diazoacetyl group converts the group to the electron-donating carboxymethyl group, causing the calcium ion efficiency to increase 25 to 50 fold. These chelators when incorporated into rat fibroblasts either by microinjection or by incubation as the membrane-permeable, enzymatically-labile tetraacetoxymethyl ester and flash-photolyzed cause a drop in intracellular free calcine ion to or below resting valves of about $10^{-7}$ M. These chelators are used to generate controlled fast removal of intracellular free calcium ion to mimic or modulate a number of important cellular responses, especially in nerve or muscle.

12 Claims, 11 Drawing Sheets

SCHEME I

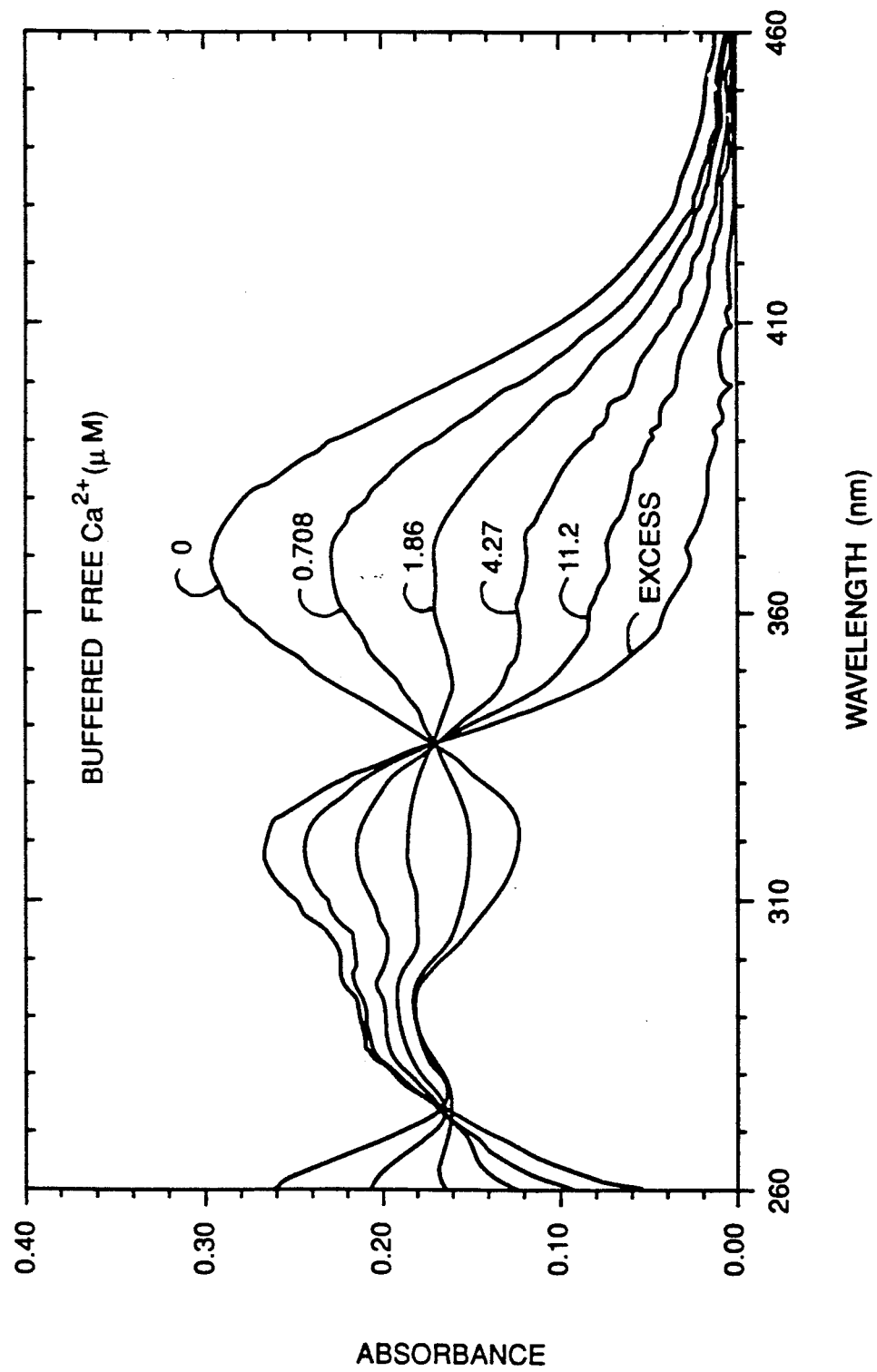
FIG._1A

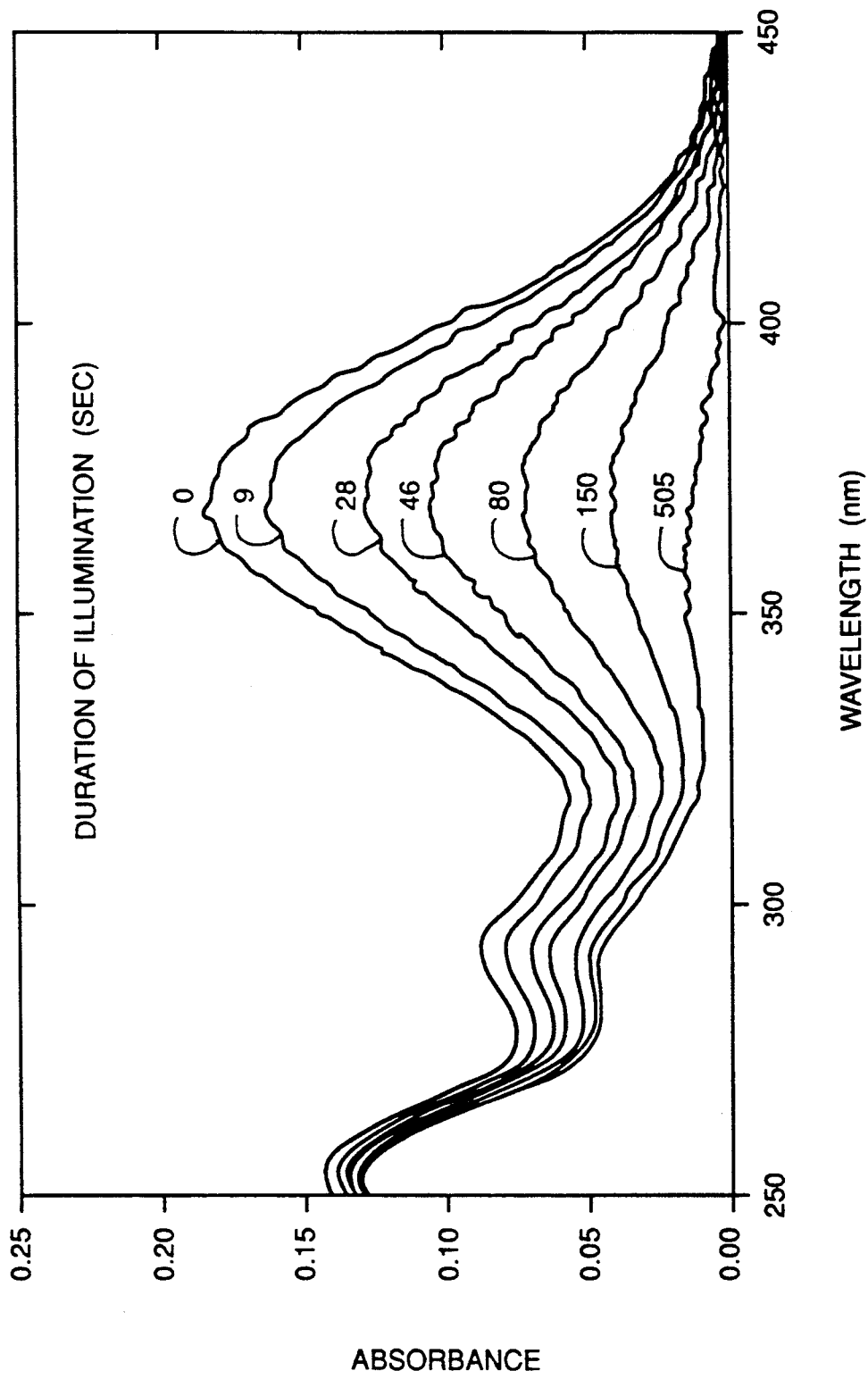
FIG._1B

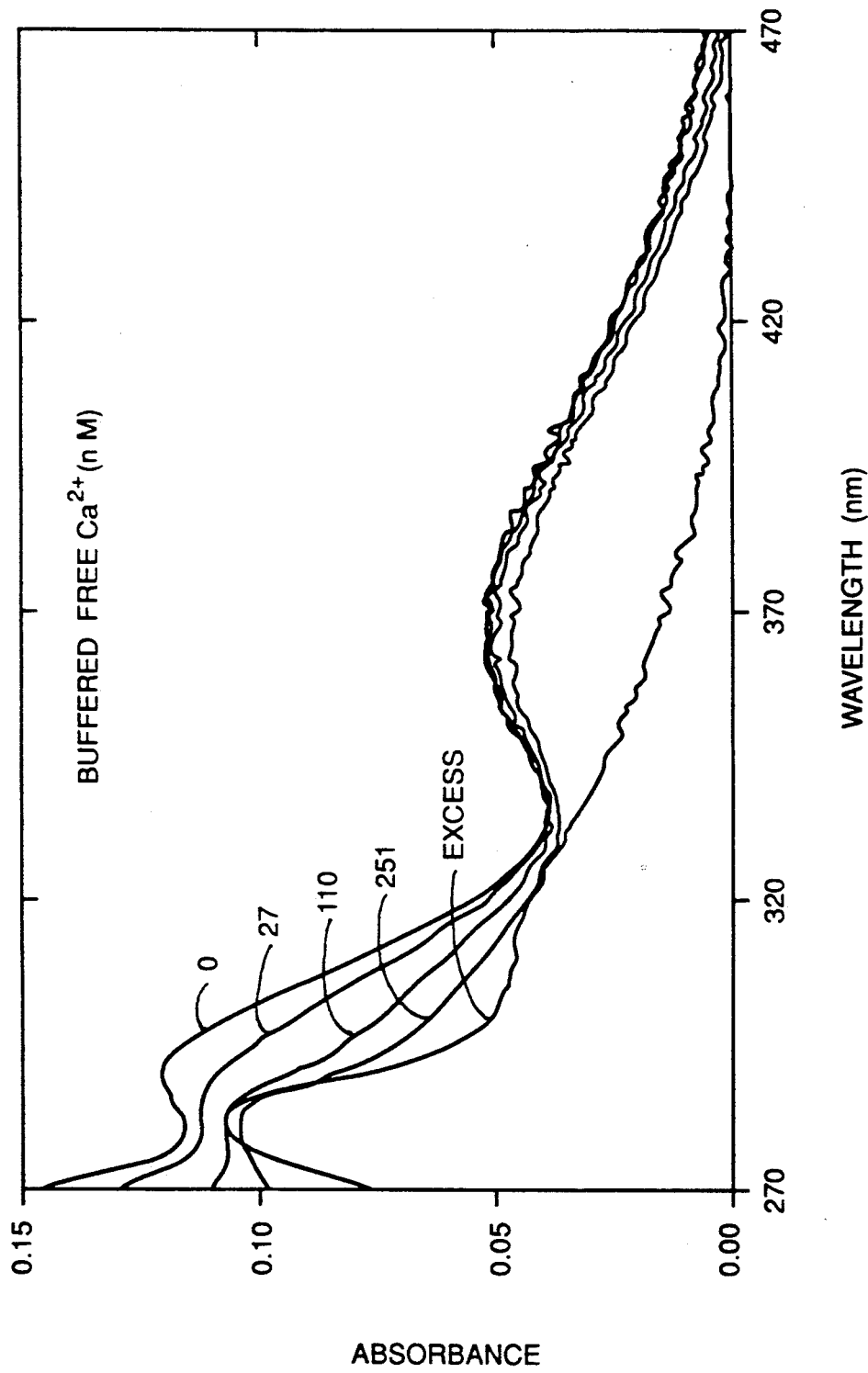

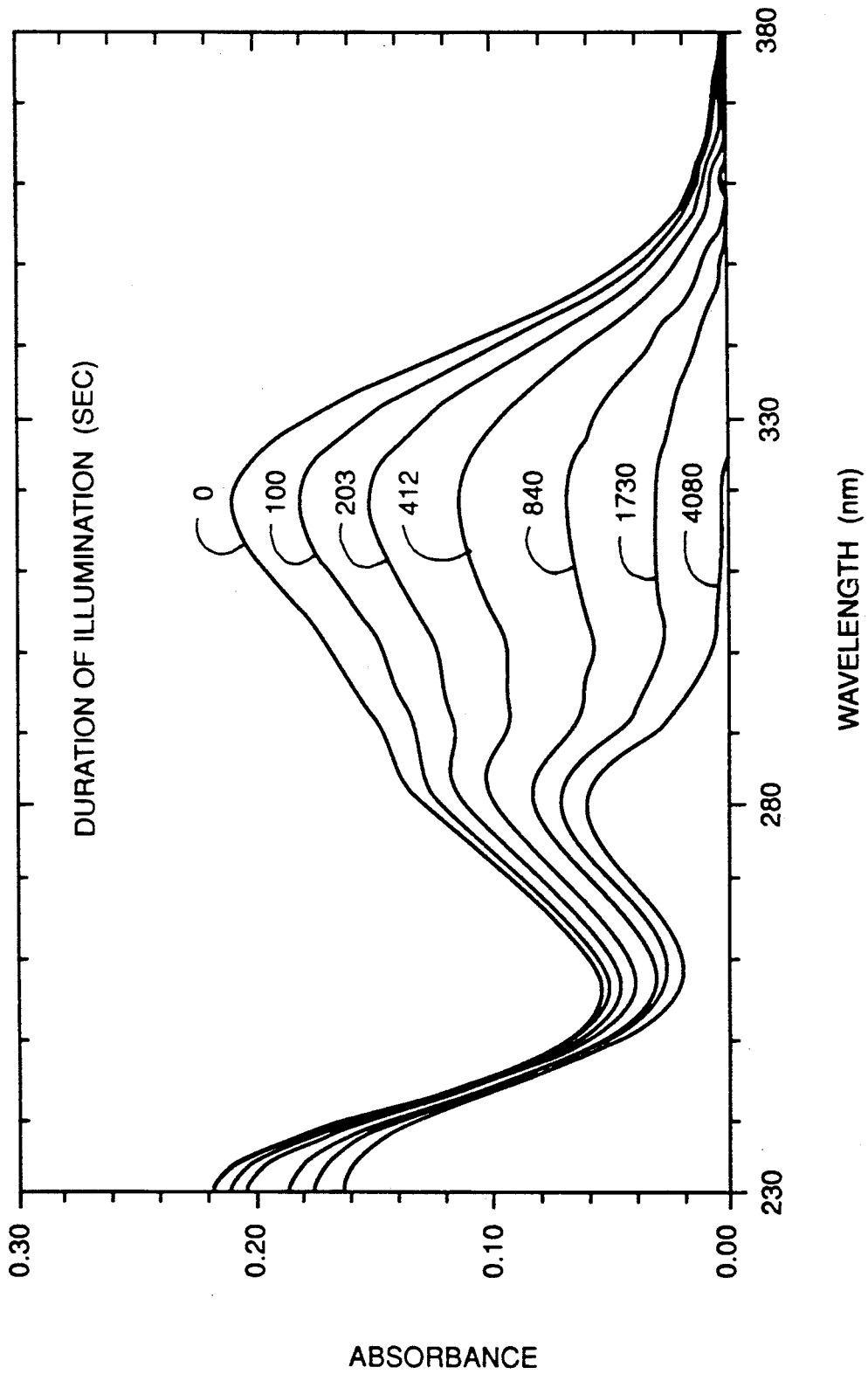
FIG._1D

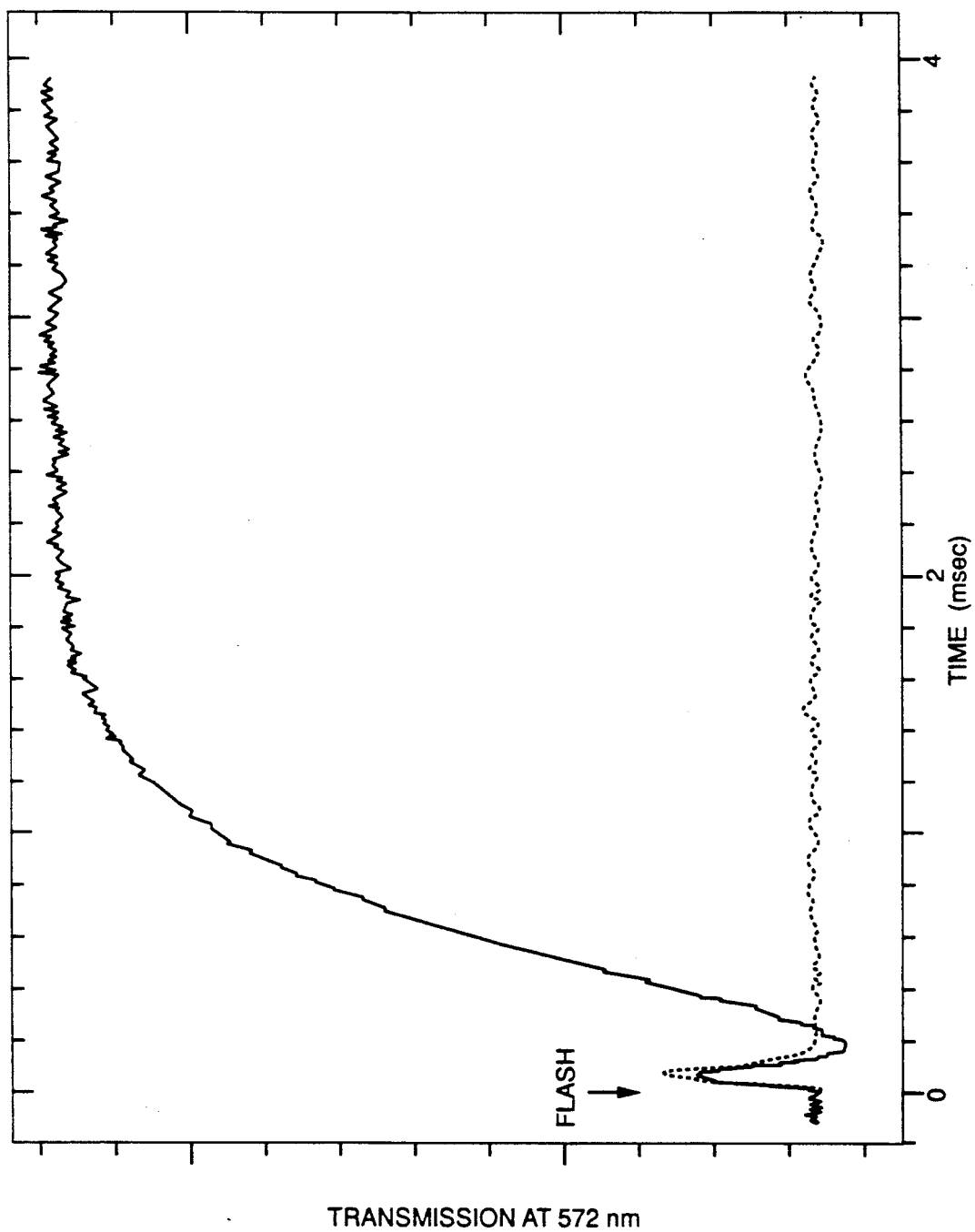
FIG._2A

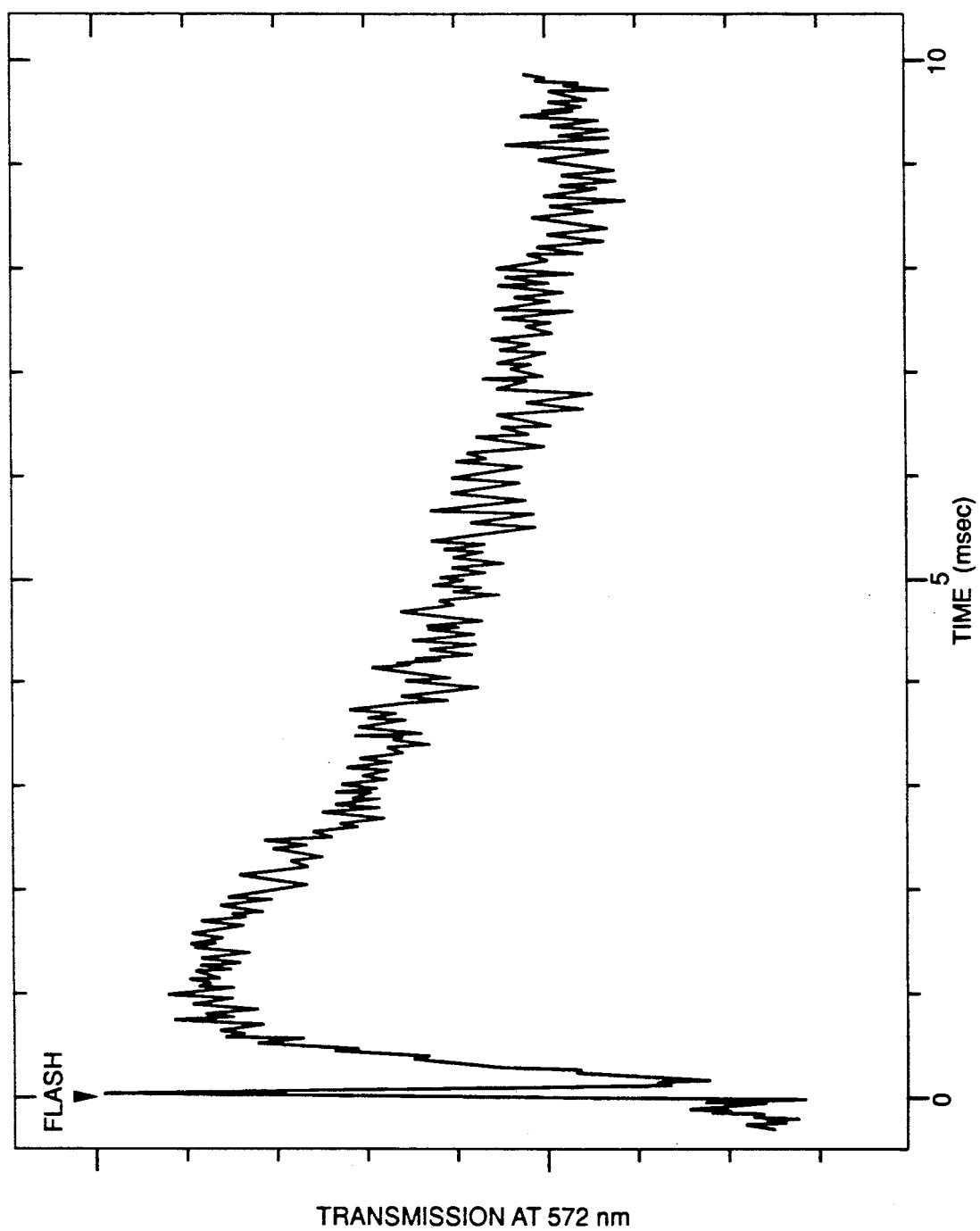
FIG._2B

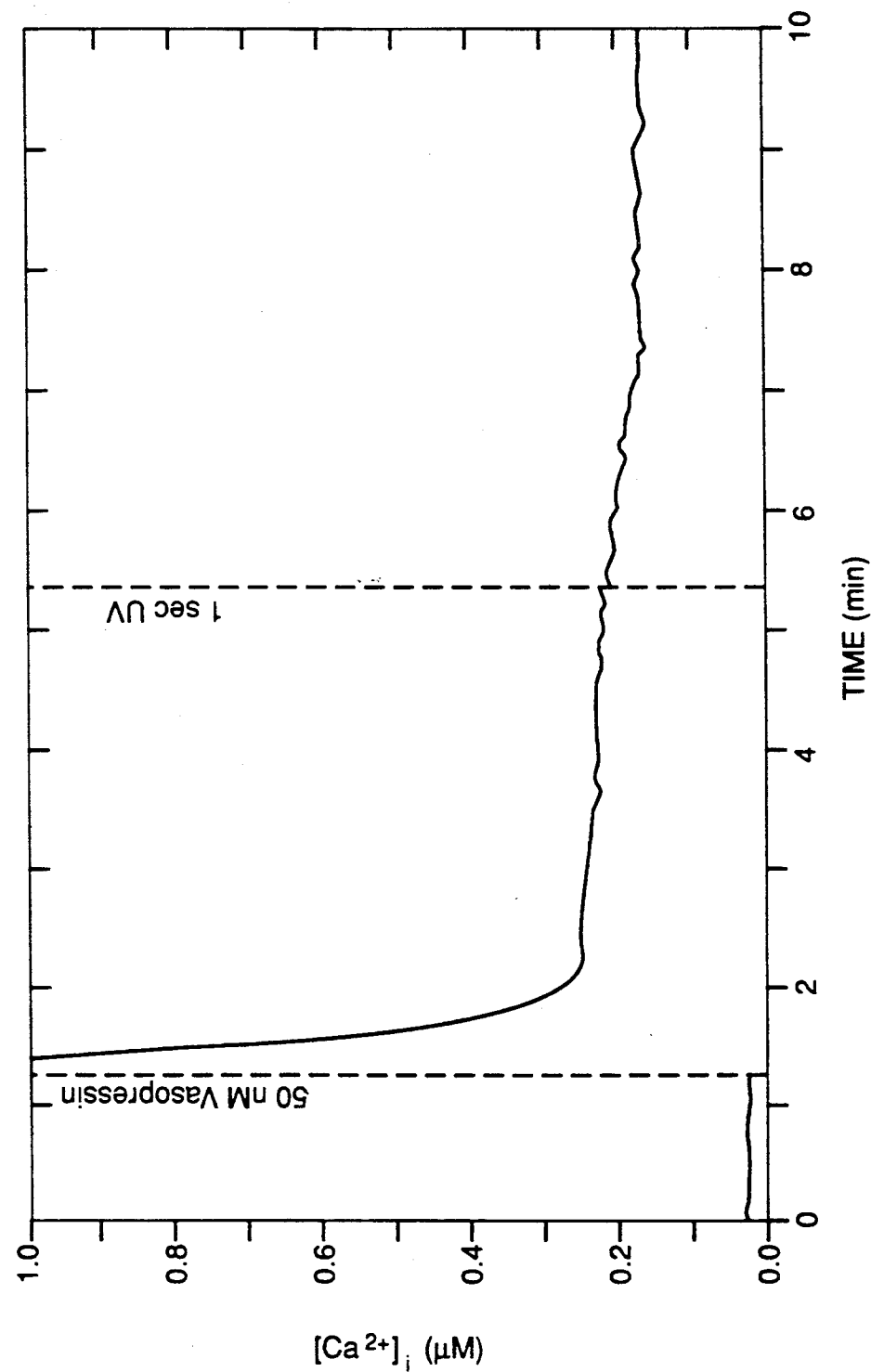
FIG._3B

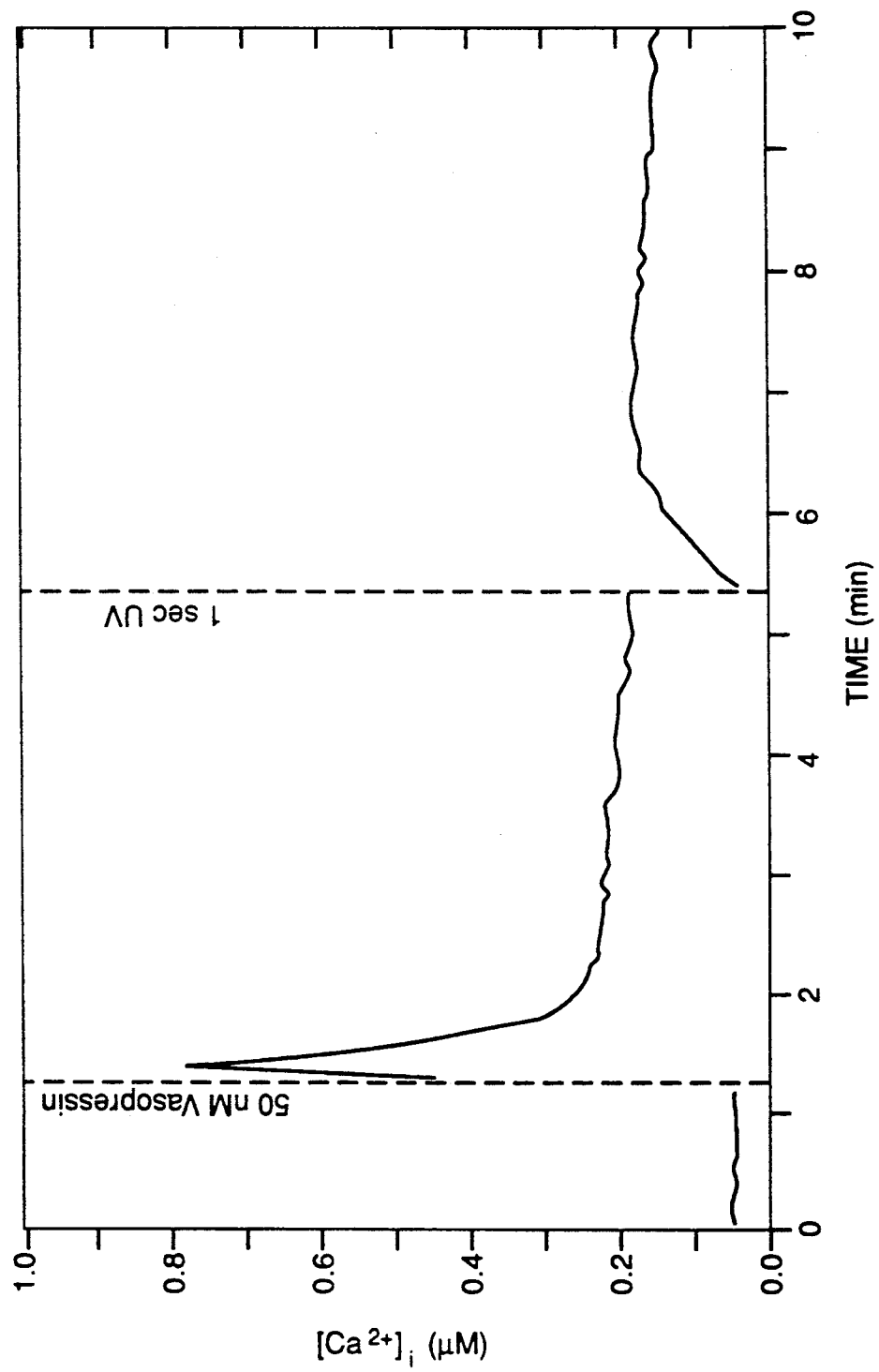
FIG._3A

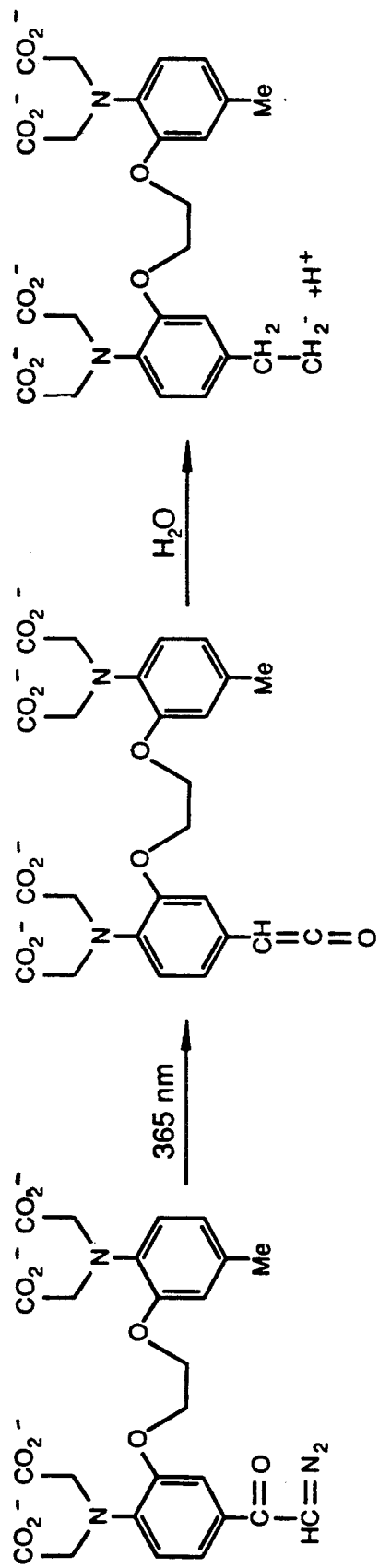
FIG._4 SCHEME I

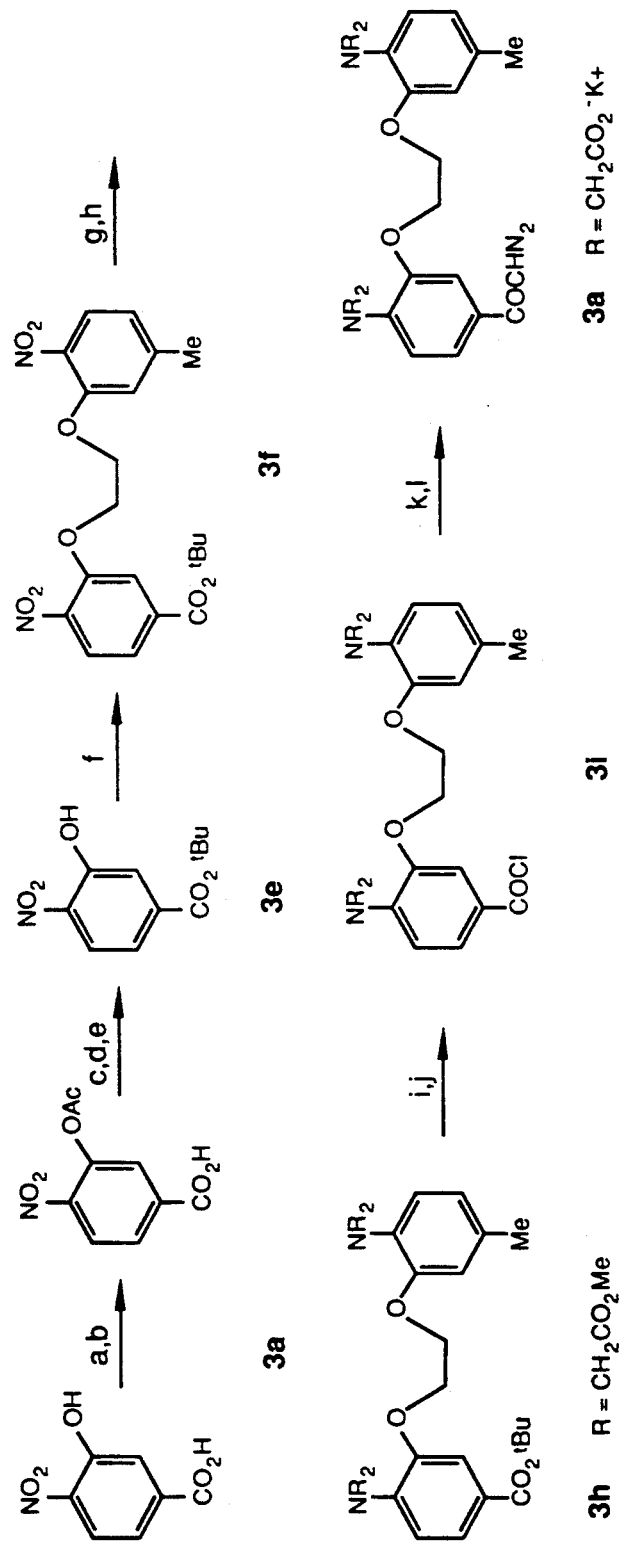
FIG._5
SCHEME III[a]
[a]Synthesis of diazo-2.
(a) Ac$_2$O, pyridine. (b) Aqueous NaHCO$_3$. (c) SOCl$_2$. (d) t-BuOH, pyridine, CHCl$_3$. (e) Aqueous NaHCO$_3$ + MeOH. (f) 1-Bromo-2-(5-methyl-2-nitrophenoxy)ethane, K$_2$CO$_3$, DMF. (g) H$_2$, catalytic Pd/C, EtOAc/EtOH, 1 atm, 20°C. (h) BrCH$_2$CO$_2$Me, 1,8-bis(dimethylamino)naphthalene (Proton Sponge, Aldrich). (i) CF$_3$CO$_2$H, CH$_2$Cl$_2$. (j) (COCl)$_2$, CH$_2$Cl$_2$. (k) CH$_2$N$_2$, Et$_2$O. (l) Aqueous KOH + MeOH.

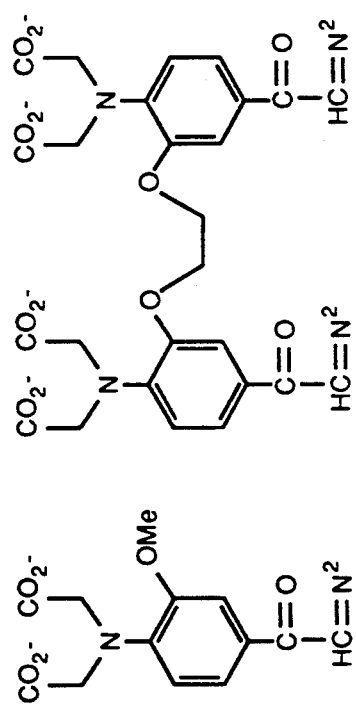
FIG._6
5a Diazo-3
4a Diazo-3
SCHEME IV

CHELATORS WHOSE AFFINITY FOR CALCIUM ION IS INCREASED BY ILLUMINATION

ORIGIN OF THE INVENTION

The present invention resulted from research with U.S. Government support under NIGMS-GM 31004 and NEI-EY 4372 awarded by the U.S. Department of Health and Human Resources. The U.S. Government has certain rights in this invention.

FIELD OF THE INVENTION

The present invention relates to photosensitive calcium ion ($Ca^{-2}$) chelators whose affinity for calcium is increased by illumination. More specifically, the present invention concerns the illumination of novel compounds, e.g. tetraacetic acid substituted anilines which bear one or more diazocarbonyl substituents and are connected by an alkylene or cyclic alkylene ether linkage. The preparation of these novel compounds is described herein.

DESCRIPTION OF RELATED ART

The recent introduction of photosensitive derivatives of nucleotides, inositol polyphosphates, neurotransmitters, calcium and protons which release the physiologically active compound with a flash of light, has enabled the dynamics of biological responses to be probed non-invasively within cells on a microsecond or millisecond time scale. The photochemical manipulation of intracellular free $Ca^{2-}$ concentration ($[Ca^{2-}]_i$) first become possible with the introduction of the "nitr" series of chelators which release $Ca^{2-}$ upon illumination with long wavelength UV light. See for example, R. Y. Tsien, et al., U.S. Pat. Nos. 4,589,432 and 4,806,604. Thus, when loaded into cells either through microinjection or through incubation with the membrane-permeant acetoxymethyl ester, the nitr compounds can be irradiated to generate spikes or plateaus of elevated $[Ca^{2-}]_i$. For example, nitr-5 has been used in cultured rat sympathetic neurons to study the activation stoichiometry and kinetics of the $Ca^{2-}$-activated $K^-$-conducting channel, and in skeletal muscle to examine the kinetics of $Ca^{2-}$ regulation of troponin C.

The present invention describes synthesis, characterization and biological application of a series of chelators whose $Ca^{2-}$ affinity is increased upon photolysis, an effect which is opposite to that exhibited by the "nitr" series of photolabile $Ca^{2+}$ chelators. Therefore, these chelators can prevent or truncate a rise in $[Ca^{2+}]$. The new series of chelators (sequestering agents), like the nitr series, are based on the parent $Ca^{2-}$ chelator, BAPTA and retain its high selectivity for $Ca^{2+}$ over $Mg^{2-}$, its insensitivity to pH variations above pH 7, and its fast $Ca^{2-}$ binding kinetics.

The ideal "caged" $Ca^{2-}$ chelator should fulfill the following requirements:

(1) The initial $Ca^{2-}$ affinity of the chelator before photolysis should be as weak as possible but certainly with dissociation constant $K_d$ greater than $10^{-6}M$;

(2) After photochemical conversion, the chelator $K_d$ should be at or below $10^{-7}M$ to match the resting $[Ca^{2-}]_i$ found in nearly all cells;

(3) The photochemistry and $Ca^{2-}$ uptake should be complete in $\leq 10^{-3}$ s;

(4) The wavelength and intensity of the light required for photolysis should not significantly perturb the cells; and (5) The photochemistry should not generate toxic byproducts or other biologically active substances.

The present invention achieves the above requirements.

DESCRIPTION OF THE RELATED ART

The following art is of general and specific interest in this application.

1. J. H. Kaplan, et al. (1978), *Biochemistry*, Vol. 17, p. 1929-1935.
2. J. A. McCray, et al. (1980), *Proc. Natl. Acad. Science U.S.A.*, Vol. 77, p. 7237-7241.
3. J. M. Nerbonne, et al. (1984), *Nature (London)*, Vol 310, p. 74-76.
4. J. W. Walker, et al. (1988), *J. Am. Chem. Soc.*, Vol. 110, p. 7170-7177.
5. J. W. Walker, et al. (1987), *Nature (London)*, Vol. 327, p. 249-252.
6. J. W. Walker, et al. (1986), *Biochemistry*, Vol. 25, 1799-1805.
7. R. Y. Tsien, et al. (1986), *Biophys. J.*, Vol. 50, p. 843-853.
8. S. R. Adams (1988), *J. Am. Chem. Soc.*, Vol. 110, p. 3212-3220.
9. G. C. R. Ellis-Davies, et al. (1988), *J. Org. Chem.*, Vol. 53, p. 1966-1969.
10. J. H. Kaplan, et al. (1988), *Proc. Natl. Acad. Sci. U.S.A.*, Vol. 85, p. 6571-6575.
11. J. A. McCray, et al. (1985), *Biophys. J.*, Vol. 47, p. 406a.
12. A. M. Gurney, et al. (1987-A), *Physiol. Rev.*, Vol. 67, 583-617.
13. A. M. Gurney, et al. (1987-B), *Proc. Natl. Acad. Sci. U.S.A.*, Vol. 84, p. 3496-3500.
14. C. C. Ashley, et al. (1987), *Physiol. (London)*, Vol. 390, p. 144P.
15. A. Minta, et al. (1989), *J. Biol. Chem.*, Vol. 264, p. 8171-8178.
16. J. P. Y. Kao, et al. (1989), *J. Biol. Chem.*, Vol. 264, p. 8179-8184.
17. A. T. Harootunian, et al. (1988), *Cold Spring Harbor Symp. Quant. Biol.*, Vol. 53, p. 935-943.
18. R. Y. Tsien (1980), *Biochemistry*, Vol. 19, p. 2396-2404.
19. R. W. Binkley, et al. (1984), *In Synthetic Organic Photochemistry*; W. M. Horspool, Ed.; Plenum: New York, New York, p. 375-423.
20. V. N. R. Pillai (1987), *Organic Photochemistry*, Vol. 9; Padwa, A.; Ed.; Dekker: New York, New York, pp. 225-323.
21. J. A. Barltrop, et al. (1986), *J. Chem. Soc., Chem. Commun.*, p. 822-823.
22. A. Patchornik, et al. (1970), *J. Am. Chem. Soc.*, Vol. 92, p. 6333-6335.
23. B. Amit, et al. (1973), *Tetrahedron Lett.*, p. 2205-2208.
24. B. Amit, et al. (1976-A), *J. Am. Chem. Soc.*, Vol. 98, p. 834-844.
25. B. Amit, et al. (1976-B), *J. Chem. Soc. Perkin Trans.*, Vol. 1, p. 57-63.
26. H. Schupp, et al. (1987), *J. Photochem.*, Vol. 36, p. 85-97.
27. Q. Q. Zhu, et al. (1987), *J. Photochem.*, Vol. 39, p. 317-322.

28. D. H. R. Barton, et al. (1971). *J. Chem. Soc. (C)*, p. 721-728.
29. V. V. Ershov, et al. (1981) in *Quinone Diazides, Studies in Organic Chemistry*, Vol. 7; Elsevier: New York.
30. H. Meir, et al. (1975) *Angew. Chem. Int. Ed. Engl.*, Vol. 14, p. 32-43.
31. H. Zimmer, et al. (1971), *Chem. Rev.*, Vol. 71, p. 229-246.
32. L. Horner, et al. (1962), *Chem. Ber.*, Vol. 95, p. 1206-1218.
33. D. G. Lee (1969), in *Oxidation*; Augustine, R. L.; Ed.; Dekker: New York, New York; pp. 81-86.
34. G. A. Olah, et al. (1964), in *Friedel-Crafts and Related Reactions*; Olah, G. A.; Ed.; Interscience: New York (1964), Vol. 3, pp. 1257-1273.
35. C. F. Bernasconi (1976), *Relaxation Kinetics*: Academic Press: New York, New York, pp. 12-13.
36. R. T. Cummings, et al. (1988), *Tetrahedron Lett.*, Vol 29, 65-68.
37. G. A. Kraft, et al. (1988), *J. Am. Chem. Soc.*, Vol. 110, p. 301-303.
38. D. Döpp (1975), *Top. Curr. Chem.*, Vol. 55, p. 49-85.
39. W. Kirmse, et al. (1959), *Justus Liebigs Ann. Chem.*, Vol. 625, p. 34-43.
40. G. Grynkiewicz, et al. (1985), *J. Biol. Chem.*, Vol. 260, p. 3440-3450.
41. E. Bothe, et al. (1976), *Angew. Chem. Int. Ed. Engl.*, Vol. 15, p. 380-381.
42. J. P. Y. Kao, et al. (1988), *Biophys. J.*, Vol. 53, p. 635-639.
43. A. P. Jackson, et al. (1987), *FEBS Lett.*, Vol. 216, p. 35-39.
44. R. Y. Tsien (1983), *Annual Rev. Biophys. Bioeng.*, Vol 12, p. 91-116.
45. R. Y. Tsien, et al. (1982), *J. Cell. Biol.*, Vol. 94, p. 325-334.
46. K Tanigaki, et al. (1987) *J. Am. Chem. Soc.*, Vol. 109, p. 5883-5884.
47. W. Lawson, et al. (1924), *J. Chem. Soc.*, Vol. 125, p. 626-657.
48. G. M. Robinson, et al. (1914), *J. Chem. Soc.*, Vol. 105, p. 1456-1469.
49. H. E. Baumgarten, et al. (1981), *J. Heterocyclic Chem.*, Vol. 18, p. 925-928.
50. W. E. Noland, et al. (1964), *J. Am. Chem. Soc.*, Vol. 29, p. 947-948.
51. A. P. Terent'ev, et al. (1959), *J. Gen. Chem. U.S.S.R.*, Vol. 29, p. 2504-2512.
52. W. B. Gall, et al. (1955), *J. Org. Chem.*, Vol. 20, p. 1538-1544.
53. W. Moser, et al. (1968), *J. Chem. Soc. (A)*, p. 3039-3043.
54. A. E. Martell, et al. (1964), *Critical Stability Constants*, Plenum: New York, Vol. 1.
55. S. W. Provencher (1976-A), *Biophys. J.*, Vol. 16, p. 27-41.
56. S. W. Provencher (1976-B), *J. Chem. Phys.*, Vol. 64, p. 2772-2777.
57. R. Y. Tsien (1989), *Ann. Rev. Neuroscience*, Vol. 12, p. 227-253.

M. A. Ferenczi, et al. (1989), Cambridge Meeting of the Physiological Society of Great Britain (Jul. 21-26, 1989), Abstract 10, p. 163P discloses the use of monoester of the tetracarboxylic acid BAPTA to produce a compound whose affinity for calcium ion is increased upon laser flash photolysis. Also see, Tsien, et al., U.S. Pat. Nos. 4,603,209, 4,689,432 and 4,806,604.

All of the references and patents cited herein are expressly incorporated by reference in this application.

It is an object of the present invention to use the adjustment of the $Ca^{2+}$ affinity of BAPTA by suitable substitution on the benzene rings present. New chelators (e.g., the diazo series) incorporate an electron-withdrawing diazoacetyl group which on photolysis undergoes the Wolff rearrangement via the ketene to produce the electron-donating carboxymethyl substitutent. Therefore, a chelator with an initially low affinity for $Ca^{2+}$ is photochemically converted to one having high affinity without steric modification of the metal binding site.

SUMMARY OF THE INVENTION

The present invention relates to compounds whose affinity for calcium ion is increased by exposure to electromagnetic radiation. Specifically, compounds are described which are structurally similar to BAPTA having at least one electron-withdrawing substituent, on one phenyl ring of BAPTA which is in the para position to the amino group, which is converted into an electron-donating group using ultraviolet irradiation.

More specifically, the substituted BAPTA-like compounds have at least one diazocarbonyl (typically diazoacetyl) group in the para-position to the amino group which is photochemically rearranged to the electron-donating carboxymethyl group, causing the $Ca^{2+}$ affinity to increase between about 20 to 100 fold.

Thus, the present invention relates to a compound of the formula:

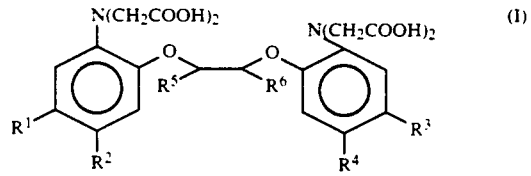

and the salts (optionally pharmacologically and/or pharmaceutically acceptable) and the esters thereof, wherein:

$R^1$ and $R^3$ are each independently selected from —H, —OH, —CH$_3$, —F, —Cl, —Br, —I, —COOH, —CN, —NO$_2$ or —NHR$^7$ wherein $R^7$ is independently selected from —H, methyl, or ethyl;

$R^2$ is —(C=O)CR$^8$=N=N, wherein $R^8$ is independently selected from —H, C1—C4 alkyl, phenyl, —COOH, —COOR$^7$, —(C=O)CH$_3$, or —CF$_3$;

$R^4$ is selected from $R^2$, —H, —CH$_3$, —CH$_2$CH$_3$, —F, —Cl—, —Br, —I, —COOH, —CN or —NO$_2$;

$R^5$ and $R^6$ are each independently selected from —H, —CH$_3$, —C$_2$H$_5$, phenyl, or —CH$_2$OH, or $R^5$ and $R^6$ together form —(CH$_2$)$_m$—Y—(CH$_2$)$_n$— where m and n are each independently 1 or 2, and Y is selected from —CH$_2$—, —O—, —NHR$^7$, —S— or —S—S—.

In another aspect the present invention relates to a method for the sequestering of calcium ion in solution, which method comprises:

(a) contacting a sample containing calcium ion with an effective quantity of the generic compound of structure (I) described above;

(b) irradiating the solution obtained with electromagnetic radiation effective to convert the diazo moiety and obtain the active calcium ion chelating agent.

BRIEF DESCRIPTION OF THE FIGURES

FIG. 1A shows absorbance spectra of unphotolyzed diazo-2 and the photochemical reaction sequence by which ultraviolet light converts it to a chelator which has a high affinity for $Ca^{2+}$ (see FIG. 3 and FIG. 4) as a function of free $[Ca^{2+}]_i$.

FIG. 1B shows the absorbance spectra of diazo-2 undergoing photolysis in the absence of $Ca^{2+}$.

FIG. 1C shows absorbance spectra of photolyzed diazo-2 as a function of free $[Ca^{2+}]_i$.

FIG. 1D shows absorbance spectra during photolysis of the $Ca^{2+}$ complex of diazo-2.

FIG. 2A is a flash photolysis record showing the kinetics of generating high affinity chelator as signaled by acid release following flash photolysis of diazo-2.

FIG. 2B is a flash photolysis record showing the kinetics of $Ca^{2+}$ uptake upon photolysis of diazo-2.

FIG. 3A shows a record of the rapid $Ca^{2+}$ sequestration by flash-photolyzed diazo-2 in a Fisher rat embryo fibroblast cell.

FIG. 3B shows a record of a control experiment to show that the $[Ca^{2+}]_i$ drop in FIG. 3A required the entire $Ca^{2+}$ binding site in diazo-2.

FIG. 4 shows one reaction sequence used to produce compounds of the present invention.

FIG. 5 shows the chemical structures of diazo-3 and diazo-4.

FIG. 6 shows the photolysis of diazo-2 at 365 nm.

DETAILED DESCRIPTION OF THE INVENTION AND PREFERRED EMBODIMENTS

As used herein:

"BAPTA" refers to 1,2-bis(ortho-aminophenoxy)ethane-N,N,N',N'-tetraacetic acid:

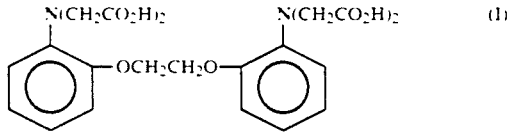

"$[Ca^{2+}]_i$" refers to cytosolic free $Ca^{2+}$ concentration;

"diazo-2" is 1-(2-bis(carboxymethyl)amino-5-methyl)phenoxy-2-(2-bis(carboxymethyl)amino-5-(diazoacetyl)phenoxy) ethane;

"diazo-2/AM" refers to the tetraacetoxymethyl ester of diazo-2;

"diazo-3" is 2-methoxy-4-(diazoacetyl)aniline-N, N-diacetic acid or is named 2-bis(carboxymethyl)amino-5-(diazoacetyl)anisole;

"diazo-3/AM" refers to diacetoxymethyl ester of diazo-3;

"diazo-4" is 1,2-bis(2-bis(carboxymethyl)amino-5-(diazoacetyl)phenoxy)ethane;

"EGTA" refers to ethylenebis(oxyethylenenitrilo)-tetraacetic acid, or ethylene glycol bis(2-aminoethyl ether)-N,N,N',N'-tetraacetic acid;

"fluo-3/AM" refers to the pentaacetoxymethyl ester of fluo-3;

"HEEDTA" refers to N-(2-hydroxyethyl)ethylenediamine-N,N',N'-triacetic acid;

"HEPES" refers to N-2-hydroxyethylpiperazine-N'-2-ethane sulfonic acid;

"PHARMACOLOGICALLY ACCEPTABLE SALT AND/OR ESTER" refers to a chemical derivative or compound of structure (I) which is recognized in the art as being useful to determine the pharmacology of a compound. It may or may not be pharmaceutically acceptable and/or non-toxic;

"PHARMACEUTICALLY ACCEPTABLE SALT" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, benzoic acid, fumaric acid, tartaric acid, citric acid, benzoic acid, cinnamic acid, mandelic acid, menthanesulfonic acid, ethanesulfonic acid, p-toluene-sulfonic acid, salicylic acid and the like;

"PHARMACEUTICALLY ACCEPTABLE ESTER" of the compound of formula I which may conveniently be used in therapy includes those containing the alkanoyloxy group, —O—C(=O)—Z, wherein is an alkyl group containing 1 to 12 carbon atoms, which is attached to carbon atom 2 of the propylene linkage instead of the hydroxyl group, i.e., the hydroxy group has been esterified. The group Z may be for example, methyl, ethyl, butyl, hexyl, octyl, dodecyl and the like. This invention contemplates those compounds of formula I which are esters as described herein and at the same time are the pharmaceutically acceptable acid addition salts thereof;

"MOPS" refers 3-morpholinopropanesulfonic acid;

"SIT" refers to silicon intensified target; and

"Tris" refers to tris(hydroxymethyl)aminomethane.

The affinity of the chelator was photochemically manipulated through electronic rather than steric effects, by introducing an electron-withdrawing group, e.g., a diazoketone, onto the benzene ring in conjugation with the iminodiacetic acid moiety (FIG. 4). Before photolysis, the electron-withdrawing power of the diazoketone pulls electron density away from the amino nitrogen and inhibits chelation of the calcium cation. Photolysis of the diazoketone group causes it to undergo a Wolff rearrangement to a carbene (structure 3b), which immediately hydrolyzes to a mildly electron-donating carboxymethyl group as shown in structure 3c of FIG. 4. Donation of electron density by the ionized carboxymethyl group into the aromatic system enhances rather than inhibits $Ca^{2+}$ binding.

Initial synthetic routes to diazo-2 focused on oxidation of the readily available para-formyl BAPTA to para-carboxy BAPTA, the key intermediate (FIG. 5, Scheme III, Compound 3h), but all efficacious methods (Lee, 1969) also oxidized the sensitive amine group. Friedel-Crafts carboxylation (Olah, et al., 1964) of BAPTA tetraester with phosgene or oxalyl chloride also failed. Eventually, the para-carboxy BAPTA was constructed stepwise from 3-hydroxy-4-nitrobenzoic acid. An Arndt-Eistert reaction of the acid chloride, Compound 3i, with diazomethane yielded the ester of the desired product, diazo-2 (FIG. 5, Scheme III). Mild base saponification yielded the chelator tetraanion. Although this compound was unstable in strong aqueous base or acid (pH>13 or pH<4), it was possible to prepare concentrated aqueous solutions of the anion for microinjection into cells, as well as the tetra(acetoxymethyl)ester for non-disruptive loading via intracellular esterases.

The tetra esters of interest of structure (I) are those wherein the smaller ester grouping is independently selected from linear or branched alkyl having 1 to 6 carbon atoms or aryl having from 6 to 10 carbon atoms. Additional esters include the $(CH_3)_3Si-$ or $(CH_3)_3CSi(CH_3)_2-$ or the alpha-acyloxyalkyl groups, preferably acetoxymethyl. Alkyl groups methyl, ethyl, Diazo-4 has a diazoacetyl group incorporated into each of the benzene rings of BAPTA and gives a much larger change in affinity for $Ca^{2+}$ upon photolysis (1600-fold) at the expense of lowered quantum yield (Compound 5a, Scheme IV, Table I), which is approximately half that of diazo-2, as two diazoketone groups must be photolyzed for complete conversion.

TABLE I[a]

| Chelator | $\lambda_{max}$, nm ($\epsilon_{max} \cdot 10^{-3}$, $M^{-1}cm^{-1}$)[b] | | $K_d(Ca^{2+})$[c], $\mu M$ | | $K_d(Mg^{2+})$[d], mM | | $\Phi$[e] | | Photolysis yield[f], % | $\tau^g$, $\mu s$ | |
|---|---|---|---|---|---|---|---|---|---|---|---|
| | free | $+Ca^{2+}$ | before | after | before | after | free | $+Ca^{2+}$ | | free | $+Ca^{2+}$ |
| diazo-2 (3a) | 370 (22.2) | 320 (20.2) | 2.2 | 0.073 0.15[i] | 5.5 | 3.4 | 0.057 | 0.030 | 90 | 433 ± 44[j] | 134 ± 12[j] |
| diazo-3 (4a) | 374 (22.8) | h | h | h | h | ~20 | 0.048 | h | 0 | 239 ± 19[j] | h |
| diazo-4 (5a) | 371 (46.0) | 320 (42.3) | 89 | 0.055 | h | 2.6 | 0.015 | 0.015 | 88 | h | h |

[a]All measurements were made at 0.1–0.15M ionic strength, pH 7.0–7.4, and 20–23° C. except where noted (see the Experimental Section and FIGS. 1 and 2 for details).
[b]Absorption maxima and corresponding extinction coefficient (in parentheses) of the dominant peaks at longest wavelength.
[c]Dissociation constant for $Ca^{2+}$, i.e. $K_d(Ca^{2+}) = [Ca^{2+}][free\ chelator]/[Ca^{2+}\text{-complex}]$, before and after photolysis.
[d]Dissociation constant for $Mg^{2+}$, i.e. $K_d(Mg^{2+}) = [Mg^{2+}][free\ chelator]/[Mg^{2+}\text{-complex}]$, before and after photolysis.
[e]Quantum efficiency of photolysis at zero or saturating $[Ca^{2+}]$.
[f]Yield of high affinity $Ca^{2+}$ chelator after photolysis.
[g]Time constant or reciprocal rate constant for main component of absorbance decrease of cresol red, attributed to formation of phenylacetates and H+ release after flash photolysis in zero or saturating $[Ca^{2+}]$.
[h]Not determined
[i]Measurement made at 0.25M ionic strength (0.2M KCl, 0.05M NaCl) at 18° C.
[j]An additional fast alkalinization component was present whose rate could not be determined accurately propyl or butyl (all isomers) are preferred.

Absorbance, $Ca^{2+}$-Binding, Photolysis and Quantum Yield

Because of the direct conjugation of the dialkylamine moiety with the diazoketone group, diazo-2 has a large absorbance in the 350–400 nm range, which shifts 50 nm to shorter wavelengths on binding $Ca^{2+}$ (FIG. 1A). The dissociation constant for $Ca^{2+}$ is relatively high, at 2.2 $\mu M$, due to the electron withdrawing ability of the carbonyl group. Photolysis occurs at 365 nm with a quantum yield of 0.030. The peak at 37 nm in zero $Ca^{2+}$ decreases to near baseline giving a spectrum similar to that of unsubstituted BAPTA, although a small peak remains at 355 nm (FIG. 1B). Binding of $Ca^{2+}$ now produces absorbance changes similar to those observed with BAPT ((FIG. 1C), interestingly, the peak at 355 nm is only affected by $>10^{-6}M$ $Ca^{2+}$. A Hill plot indicates an affinity of about 73 nM after photolysis for Compound 3c (FIG. 4, Scheme I), in which the carboxymethyl substituent is weakly electron-donating. Some deviation of the plots from linearity suggests a side product with a dissociation constant of about $10^{-6}M$. The expected side product of the Wolff rearrangement is the para-(2-hydroxyacetyl) derivative formed through insertion of the intermediate carbene into the O—H bond of water. The reaction of diazo-2 with dilute aqueous acid should give the same product whose absorbance spectrum indeed matched that of the residual peak at 355 nm after photolysis in low $Ca^{2+}$. Dilute acid probably converts the diazoketone quantitatively to the hydroxyacetyl derivative, since the process shows sharp isobestic points, and the resulting product displays complete lack of photosensitivity. Once the extinction coefficient for the hydroxyacetyl derivative was known, the amount of the side product arising from photolysis is calculated to be about 10%.

Diazo-3 was synthesized as a control for any deleterious effects of the intermediate ketocarbene or acid release from the phenylacetic acid product in biological experiments with diazo-2. Diazo-3 contains the photosensitive moiety of diazo-2 but, lacking half of the cation coordinating site (Compound 4a, Scheme IV), has negligible affinity for $Ca^{2+}$ ($K_d > 10^{-3}M$, see Table I).

Compounds wherein $R^8$ is not —H: To prepare diazocarbonyl compounds with $R^8 = C_1$–$C_4$ alkyl, phenyl, carboxy, or alkoxycarbonyl, one employs the $C_2$–$C_5$ diazoalkane, phenyldiazomethane, diazoacetic acid or diazoacetic ester in place of unsubstituted diazomethane. To prepare diazocarbonyl compounds with electron-withdrawing $R^8$ groups such as $COOR^7$, —$COCH_3$, or —$CF_3$, an alternative route is to react the acid chloride (i.e. structure 3i of FIG. 5) with any of a variety of carbanionic synthons equivalent to $\ominus CH_2COOR^7$, $\ominus CH_2COCH_3$, or $\ominus CH_2CF_3$, respectively. The diazo group is then introduced by the known reaction of diazo transfer (see J. March, *Advanced Organic Chemistry*, 3rd ed., John Wiley, 1985, pp. 534–535) from p-toluenesulfonyl azide to the active methylene group.

Compounds where $R^5$ and $R^6$ are not equal to —H: These compounds are synthesized by combining the teachings of U.S. Pat. No. 4,806,604 and the present invention in the following manner by those skilled in this art. For example, the compound with $R^1 = R^3 = H$, $R^5 = R^6 = -(CH_2)_3-$, $R^2 = -COCHN_2$, and $R^4 = Me$ is synthesized as follows: The route leading to compound Va of U.S. Pat. No. 4,806,604 is performed using t-butyl-3-fluoro-4-nitrobenzoate in place of the 2-fluoronitrobenzene originally used between compounds Ia and IIIa described in that patent. The resulting compound has an extra t-butoxy-carbonyl group added to the structure of Va. It would therefore be equivalent to structure 3h of FIG. 5 of the present invention, but with $R^5$ and $R^6$ equal to $-(CH_2)_3-$ instead of $R^5 = R^6 = H$. This compound is converted to the final diazoketone in which $R^5$ and $R^6 = -(CH_2)_3-$ in analogy to the conversion of 3h to 3a when $R^5 = R^6 = -H$ described herein.

In a further embodiment, the symmetrical analog of diazo-4 in which $R^1 = R^3 = H$, $R^5 = R^6 = -(CH_2)_4-$, $R^2 = R^4 = -COCHN_2$ is prepared by reacting cis-cyclohexane-1,2-diol with 2 equivalents of t-butyl-3-fluoro-4-nitrobenzoate, followed by reduction of the nitro groups and alkylation of the resulting amino groups with methyl bromoacetate as taught in U.S. Pat.

No. 4,806,604. The t-butyl groups are hydrolyzed and both benzoic acid groups converted to acid chlorides and reacted with diazomethane as in the preparation of diazo-4 as described herein.

Preferred compounds of structure (I) include those wherein $R^8$ is hydrogen.

More preferred compounds are those wherein R4 is selected from —H, —CH$_2$ or —R$^2$, when $R^8$ is hydrogen.

Additional preferred compounds are those wherein $R^4$ is —(C=O)CR$^8$=N=N, and $R^8$ is hydrogen.

Especially preferred compounds are those wherein $R^1$ and $R^3$ and $R^5$ and $R^6$ are each —H, preferably when $R^4$ is —CH$_3$.

Preferred cyclic structures of compound I include those wherein $R^5$ and $R^6$ together form —(CH$_2$)$_m$—Y—(CH$_2$)$_n$— where m is 1, n is 1, and Y is —CH$_2$—; or wherein $R^5$ and $R^6$ together form —(CH$_2$)$_m$—Y—(CH$_2$)$_n$— where m is 2, n is 1, and Y is —CH$_2$6—; or wherein $R^5$ and $R^6$ together form —(CH$_2$)$_m$—Y—(CH$_2$)$_n$— where m is 1, n is 1, and Y is O or S, especially when $R^4$ is —(C=O)CHH—N=N or —CH$_3$.

The method to chelate $Ca^{2+}$ in solution using the preferred embodiments described herein above is also claimed.

The affinity of diazocarbonyl compounds for $Mg^{2+}$ is weak and changes only 1.67-fold upon photolysis, so that perturbations of intracellular free [$Mg^{2+}$] are expected to be negligible. The quantum yield for photolysis is modest, but the high extinction of 370 nm results in satisfactory rates of photolysis, several times faster than nitr-5 which has been photolyzed successfully in cells without noticeable irradiation damage. The quantum yield is consistent with reported values of diazoacetophenone when the longest wavelength absorption band (assigned to a forbidden transition) is excited (Meier, et al., 1975; Kirmse, et al., 1959). Reversing the position of the diazo and carbonyl group to produce a methoxycarbonyldiazomethyl substituent (i.e. CH$_3$O$_2$C.C(N$_2$)—) in model compounds greatly increased the quantum yield but resulted in a considerably lower extinction coefficient in the long-wavelength UV, making it an inferior chelator overall. The difference in quantum yield of the $Ca^{2+}$-free forms of diazo-2 is probably due to the deactivating effect of the para-amino group on the photochemistry, which is greatly reduced with $Ca^{2+}$-dependent behavior is analogous to that observed in the nitr chelators and to the $Ca^{2+}$-dependent fluorescence quantum yields of related indicator dyes.

Flash Photolysis Kinetics in Vitro

When a diazoketone is photolyzed in aqueous solution the major ultimate product is a carboxylic acid. In the present case, a substituted phenylacetic acid with an expected pK$_a$ close to 4.5, is generated (Compound 3c, Scheme I). Product formation is thus accompanied by proton release generated (Compound 3c, Scheme I). Product formation is thus accompanied by proton release which is readily monitored spectroscopically if a suitable acid-base indicator is used. Cresol red (pK$_a$ 8.2) is chosen to monitor proton release following flash photolysis of the diazo compounds in aqueous solutions adjusted to pH 8. FIG. 2A shows a typical diazo-2 flash photolysis trace where the transmittance of cresol red in the sample was monitored at 572 nm. The absorbance of cresol red at 572 nm decreases with decreasing pH. As the carboxylic acid product, 3c, is generated, the solution acidifies and the transmittance of the sample is expected to rise. As revealed by exponentially rising trace in FIG. 2A, a transmittance increase due to acidification was indeed the dominant effect observed following flash photolysis of diazo-2 in aqueous solution. The chemical structure of the photo-labile chromophore in diazo-3 is essentially identical to that in diazo-2 (FIG. 6, Scheme IV). Correspondingly, flash photolysis of diazo-3 under identical conditions yield experimental traces which were qualitatively the same as those obtained for diazo-2. In Table I is presented the characteristic time constants for carboxylic acid formation following flash photolysis of diazo-2 and diazo-3. Flash photolysis of $Ca^{2+}$-bound diazo-2 produced the carboxylic acid with a characteristic time of 134 $\mu$s. The time slowed to 433 $\mu$s when $Ca^{2+}$-free diazo-2 was photolyzed. Diazo-3, with negligible pre- and post-photolysis affinity for $Ca^{2+}$ ($K_d$'s > 10$^{-3}$M), yielded product with a time constant of 238 $\mu$s, intermediate between those found for the $Ca^{2+}$-bound and the $Ca^{2+}$-free forms of diazo-2.

Having determined the rate at which the high-affinity chelator was photochemically generated from diazo-2, the kinetics of $Ca^{2+}$ binding by the photolysis of diazo-2 was examined relying on the 1:1 competition between protons and $Ca^{2+}$ for the chelator HEEDTA, i.e.:

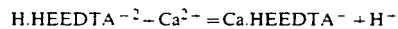

$$H.HEEDTA^{-2} + Ca^{2+} = Ca.HEEDTA^- + H^+$$

If diazo-2 is photolyzed in the presence of HEEDTA partially saturated with $Ca^{2+}$, the photo-generated Compound 3c would take some $Ca^{2+}$ away from HEEDTA. The newly freed HEEDTA would then take up some protons and lead to an alkalinization of the sample. The shift in $Ca^{2+}$-binding equilibrium is thus visualized with an indicator like cresol red. Control experiments indicate that at HEEDTA buffer concentrations $\geq$ 2 mM, the intrinsic kinetics of the $Ca^{2+}$-HEEDTA equilibrium was no longer limiting the speed of the final alkalinization.

FIG. 2B shows the flash photolysis of 70 $\mu$M diazo-2 plus 2 mM HEEDTA half-saturated with $Ca^{2+}$ to give a calculated free [$Ca^{2+}$] of 377 nM. It is noted that the solution first acidified owing to the formation and dissociation of the product carboxylic acid, but subsequently began realkalinizing as the newly formed product chelator competed with HEEDTA for $Ca^{2+}$. The time constant of the realkalinization was 2.8 ms (Table I). Since [$Ca^{2+}$] was almost perfectly clamped by the HEEDTA, this time constant should be equal ($k_{on}$[$Ca^{2+}$]+$k_{off}$)$^{-1}$, where $k_{on}$ is the bimolecular rate constant for the binding of $Ca^{2+}$ by 3c, $k_{off}$ is the unimolecular rate constant for dissociation of the complex between compound 3c and $Ca^{2+}$, and [$Ca^{2+}$] is the 377 nM free $Ca^{2+}$ concentration as set by the dominant HEEDTA buffer (Bernasconi, 1976). From equilibrium measurements on Compound 3c, we know $K_d = k_{off}/k_{on} = 73$ nM (Table I). Therefore, for photolyzed diazo-2, $k_{on} = 8.0 \times 10^8$ M$^{-1}$s$^{-1}$ and $k_{off} = 58$s$^{-1}$.

Biological Application of the Diazo Chelators

The tetraacetoxymethyl esters of diazo-2 and diazo-3 were synthesized. The acetoxymethyl (AM) groups mask the negative charges on the carboxylate functions, so the AM ester of diazo-2 and diazo-3 can easily diffuse across the cell membrane, which is largely impermeable to ions. Once inside the cell, non-specific esterases in the cell hydrolytically cleave the AM esters and restore diazo-2 and diazo-3 to their tetracarboxylate forms, which being polyanions, are trapped within the cell. By this method, cells have been shown to accumulate millimolar levels of other polycarboxylate chelators in the presence of micromolar extracellular levels of the corresponding AM ester (Tsien, et al., 1982). The results shown in FIG. 3A demonstrate that diazo-2 loaded into living cells via the AM ester sequester $Ca^{2+}$ when photolyzed. Prior to the start of data acquisition (t=0), the REF52 fibroblast cell was loaded with diazo-2 and fluo-3. Fluo-3, by incubation with their AM esters, is an indicator whose fluorescence is excited by visible wavelength light that does not affect the diazo compounds. Its fluorescence quantum yield is enhanced about 40-fold by $Ca^{2+}$ binding, which occurs with a $K_d$ of 400 nM. At the time marked in FIG. 3A by the first dashed line, the cell was stimulated with 50 nM [arg$^8$]-vasopressin, which elicited a sharp but transient rise in $[Ca^{2+}]_i$, which declined to a plateau value (about 200 nM) that was higher than the prestimulation resting $[Ca^{2+}]_i$. At the time marked by the second dashed line, the cell was illuminated with 1 second UV, which control experiments showed was sufficient to photolyze all of the diazo-2 in the cell. The $Ca^{2+}$ binding efficacy of photolyzed diazo-2 is evident as $[Ca^{2+}]_i$ dropped precipitously to about 50 nM immediately after photolysis. The cell subsequently restored $[Ca^{2+}]_i$ back up to the post-stimulation plateau level.

Diazo-2 microinjected into cells is also effective in sequestering $Ca^{2+}$ after photolysis. However, the use of AM esters eliminates the need for microinjecting living cells. Such microinjection requires considerable technical skill, always causes some injection damage, requires seconds to minutes for each individual cell, and is impossible on small, free-floating cells types.

Since diazo-2 photolysis proceeds through reactive photochemical intermediates and, at physiological pH, generates a proton for each molecule of high-affinity chelator produced, it is important to control for all the chemical effects of diazo-2 photolysis which have nothing to do with $Ca^{2+}$ chelation (sequestration). Diazo-3 is ideally suited for this purpose because except for its inability to bind $Ca^{2+}$, its chemistry is essentially identical to that of diazo-2. FIG. 3B shows results from an experiment analogous to that presented in FIG. 3A except that the cell had been loaded with diazo-3 instead of diazo-2. It can be seen from FIG. 3B that the response of the cell to [arg$^8$]-vasopressin is similar to that seen in FIG. 3A; however, UV photolysis of intracellular diazo-3 did not have any effect on the intracellular $Ca^{2+}$ concentration.

HPLC analysis revealed that when 100 μM diazo-3 was photolyzed in the presence of 100 mM lysine.HCl at pH 7.2, aside from the main peak, which was absent when diazo-3, about 6% of the total absorbance was found under a new peak which was absent when diazo-3 was photolyzed in KCl. The new peak is attributed to lysine which has been covalently modified by a reactive intermediate generated by photolysis of diazo-3. If it is assumed that the normal photoproduct and the lysine-modified photoproduct have comparable extinction coefficients, then it is calculated that about 6 μM of the modified lysine was produced, i.e. lysines were covalently modified at a frequency of about $6\times10^{-5}$.

Diazo-4, which has a diazoacetyl substituent on each of the aromatic rings of BAPTA (Compound 5a, FIG. 6, Scheme IV) and shows a much greater change in $Ca^{2+}$ affinity (1600-fold) upon complete photolysis (Table I), was made for certain biological applications which require decreasing $[Ca^{2+}]_i$ from $\geq 10^{-5}$M to about $10^{-7}$M. Diazo-2 in such circumstances would either prevent high $[Ca^{2+}]$ levels even before photolysis, or would become $Ca^{2+}$-saturated and be unable to generate free high-affinity chelator to lower $[Ca^{2+}]_i$. However, the intermediate in the photolysis of diazo-4 (in which only one diazoacetyl group is photolyzed) will have a similar affinity to unphotolyzed diazo-2, so to jump from about $10^{-5}$M to about $10^{-7}$M in free $[Ca^{2+}]$ will require almost complete photolysis of all diazo-4, whereas diazo-2 can be photolyzed partially several times in an experiment. Diazo-4 would be expected to produce 19% low-affinity side product on complete photolysis, although indeed 20% could be measured by the residual absorbance at 355 nm.

The possible kinetic limitations on using diazo-2 and diazo- in biological systems need to be considered. Since the high-affinity chelator is generated by hydrolysis of the photoproduct ketene, the rate of $Ca^{2+}$ sequestration will be limited by the rate at which the chelator is produced. Photochemical steps leading to the formation of product ketene from diazoketones are typically fast, being complete in hundreds of nanoseconds (Tanigaki, et al., 1987). The real limit is the rate at the rate at which the ketene is transferred into the carboxylic acid by hydrolysis, a process which, for diazo-2 at 20° C., has a time constant of 433 μs. Ultimately then, flash photolysis of diazo-2 or diazo-4 should be able to quench $Ca^{2+}$ rises which have rise times on the order of a millisecond or longer. Fortunately, this rate is fast enough for most biological applications.

Two potential complications need to be considered in using diazo-2 or diazo-4 in living cells and these have to do with aspects of the photochemistry of diazo-2 and diazo-4. The photolyses proceed through very reactive intermediates, ketocarbenes (which may interconvert with oxirenes), which rearrange in hundreds of nanoseconds (Tanigaki, et al., 1987) to ketenes. Since all the intermediates are highly reactive, they might covalently modify biological important substrates and perturb the normal functions of the cell. The second complication arises from the fact that at physiological pH, photolysis of diazo-2 releases a proton in addition to generating $Ca^{2+}$-buffering capacity. Although the intracellular pH is tightly regulated by the cell (millimolar levels of pH buffering exist in normal cells), small pH changes can have relatively profound effects.

The first problem, that of reactive intermediates, is probably not serious, since even in the intracellular environment, water is still by several orders of magnitude the most abundant reagent. Indeed, in experiments where 100 μM diazo-3 was photolysed in the presence of 200 mM lysine.HCl at pH 7.2, very low levels of covalent lysine modification, i.e., 6 lysines in $10^5$ were covalently modified. Acidification by the photoproduct of diazo-2 or diazo-4 is probably a more serious problem, since innumerable biochemical processes are dependent on pH. For both concerns, diazo-3 is an important control compound. Diazo-3 manifests all of the same chemical aspects as diazo-3 is an important control compound. Diazo-3 manifests all of the same chemical aspects of diazo-2 except for $Ca^{2+}$-binding. Diazo-3 is thus the ideal compound to control for all of the chemical effects of diazo-2 which are unrelated to $Ca^{2+}$ chelation. Indeed, the results shown in FIG. 3B demonstrate that photolysis of intracellularly trapped diazo-3 had no detectable effect on $Ca^{2+}$ hemeostasis in the REF52 fibroblast cell. Finally, diazo-3 is perfectly good "caged proton" in its own right, and can be used photochemically to study the effects of transient pH drops on cellular physiology. An advantage of diazo-3 over other "caged protons" (McCray, et al., 1985) is its ready loading and accumulation in cells by incubation with the cell-permeant AM ester.

DETAILED DESCRIPTION FIGS. 1A TO 3B

FIG. 1A shows the absorbance spectra of unphotolyzed diazo-2 as a function of free $[Ca^{2+}]$. The titration was done at 22° C. with 10 mL of 100 mM KCl, 10 mM K-MOPS, 10 mM $K_2H.HEEDTA$, and 14 pM diazo-2 as starting materials, adjusting the pH to 7.24, recording the spectrum, and then discarding 1.0 mL of this solution and replacing with 1.0 mL of 100 mM KCl, 10 mM K.MOPS, 10 mM KCa.HEEDTA, 14 μM diazo-2, readjusting the pH to 7.24, and recording the spectra, which was then in 9 mM K2H.HEEDTA. Subsequent iterations to reach n mM KCa.HEEDTA, (10-n) mM HEEDTA, n=2-10, were done by discarding 10.0/(11-n) mL and replacing with equal volumes of the 10mM KCa.HEEDTA, 14 μM diazo-2 stock. After n=10 had been reached to give free $Ca^{2+}$ between $10^{-5}$ and $10^{-4}$M. addition of 1 mM $CaCl_2$ had no further effect on the spectrum. For clarity only six spectra are including in the figure, n=0, 2, 4, 6, 8, and 10. Each spectrum is labeled with the calculated free $[Ca^{2+}]$ imposed by the HEEDTA buffer, assuming a log effective stability constant of 5.55 at pH 7.24.

FIG. 1B shows the absorbance spectra of diazo-2 undergoing photolysis in the absence of $Ca^{2+}$. Diazo-2 was dissolved at 8 μM in 100 mM KCl, 10 mM Tri, 5 mM MOPS, 4 Mm $K_2H_2EGTA$ and pH titrated to 7.2 with HCl. Spectra were obtained after 0, 2, 5, 9, 16, 28, 46, 80, 150, 285, 505 and 903 sec of 365-nm illumination at $7.82 \times 10^{-9}$ einsteins $cm^{-2}s^{-1}$ from Spectroline lamp. For clarity only the 0-, 9-, 28-, 46-, 80-, 150-, and 505-s spectra are reproduced herein. The 505- and 903-s spectra were identical, confirming completion of photolysis after those times. Solutions were at 22±2° C.

FIG. 1C shows the absorbance spectra of phenylacetate (photolyzed diazo-2) as a function of free $[Ca^{2+}]$. The phenylacetate was produced by irradiating a 30 μM solution of diazo-2 in 100 mM KCl, 10 mM Tris.HCl, 10 mM $K_2H.HEEDTA$, pH 8.40, with Spectroline lamp at 365 nm to completion. The titration was then performed as in A but the pH was maintained at 8.40, at which the calculated log effective stability is constant for HEEDTA was 6.60.

FIG. 1D shows the absorbance spectra during photolysis of the $Ca^{2+}$ complex of diazo-2. The method was as described in FIG. 1B except that the EGTA was replaced by 2 mM $CaCl_2$, and spectra were measured after 0-, 50-, 100-, 203-, 412-, 840-, 1730-, 4080-, and 8000-s illumination. The last two spectra were identical, confirming completion. For clarity the 50- and 8000-s spectra are omitted.

FIG. 2A shows a flash photolysis record of the kinetics of generating high-affinity chelator as signaled by acid release following flash photolysis of diazo-2. Diazo-2 was dissolved at 70 μM concentration in 100 mM KCl, 40 μM $H_4BAPTA$, and enough cresol red to yield $OD_{572}=0.1$ after the solution has been adjusted to pH 8. Transmitted light intensity at 572 nm was monitored using an HG-Xe.arc lamp, a monochromator, a photo multiplier and a Biomation transient recorder. Each small division of the ordinate corresponds to 0.002 absorbance unit. The small upward spike at time zero is an optical artifact from the xenon flash lamp. The solid trace is from the sample containing diazo-2. For comparison, the dotted trace is from a photochemically inert sample containing cresol red in 100 mM KCl at pH about 8. This control record shows that the flash artifact is clearly separable from the gradual decrease in absorbance of the cresol red as acid is released during the dark reaction following flash photolysis of diazo-2.

FIG. 2B is a flash photolysis record of the kinetics of $Ca^{2+}$ uptake by photolyzed diazo-2. The sample contained 70 μM diazo-2, 2 mM HEEDTA, 1 mM $CaCl_2$, 100 mM KCL and cresol red to give $OD_{572}=0.1$ after the solution was adjusted to pH 8 under helium purge. Monitoring the light transmission at 572 nm was performed as for A. Each small division of the ordinate corresponds to $3.4 \times 10^{-4}$ absorbance unit. The spike at time zero is an optical artifact generated by the xenon flash lamp. As the acid form of the high-affinity chelator was generated following flash photolysis, the solution transiently acidified, as revealed by the decrease in cresol red absorbance (rise in transmitted light intensity). As the photolyzed diazo-20 took $Ca^{2+}$ away from HEEDTA, the freed HEEDTA bound protons and thus alkalinized the solution, a process reflected by the increase in cresol red absorbance (i.e., decline in light transmission at 572 nm).

FIG. 3A shows a flash photolysis of the rapid $Ca^{2+}$ sequestration by flash-photolyzed diazo-2 in a Fisher rat embryo fibroblast cell. Prior to the start of data acquisition, the REF52 fibroblast cell was loaded with fluo-3 and diazo-2 by incubation for 30 min at 25° C. DME medium containing 1 μM diazo-2/AM and 10 μM fluo-3/AM. Acquisition of fluo-3 fluorescence intensity images was begun at time 0. The fluorescence intensity data was converted to intracellular $Ca^{2+}$ concentrations using a calibration procedure previously described. The event markers correspond to 1) stimulating the cell with 50 nM [$arg^8$]-vasopressin, and 2) flashing the cell for 1 s with UV light.

FIG. 3B shows a record of a control experiment to show that the $[Ca^{2+}]$ drop in (A) required the entire $Ca^{2+}$-binding site of diazo-2 and was not an artifact arising from the chemistry of diazoacetyl group photolysis. The experimental conditions were the same as in (A) except that the cell wa loaded with fluo-3 and diazo-3 (instead of diazo-2) by incubation for 90 min at 25° C. in DME medium containing 10 μm fluo-3/AM and 1M diazo-3/AM. The event markers correspond to 1) stimulating the cell with 50 nM [$arg^8$]-vasopressin, and 2) flashing the cell for 1 s of UV light.

The following Examples are presented for the purposes of illustration and description only. They are not to be construed as being limiting in any manner.

COMPOUND SYNTHESES

Chemicals and solvents (high performance liquid chromatography-HPLC-grade) were used directly as obtained unless otherwise noted. Chloroform was redistilled from $P_2O_5$, dimethylformamide and N-methyl 2-pyrrolidinone were dried over 4A molecular sieve, and thionyl chloride,, tert-butanol and pyridine were redistilled.

Proton magnetic resonance spectra ($^1$H NMR) were recorded on a Varian EM-390 90-MHz spectrometer in CDCl$_3$ unless otherwise noted, and the chemical shifts are given in δ values relative to tetramethylsilane. Ultraviolet (UV) absorbance spectra were recorded on a Cary 210 or a Perkin-Elmer Lambda Array 3840 spectrophotometer at 20°±2° C. Melting points are in Centigrade and are uncorrected. Elemental analyses were performed by the Microanalytical Laboratory in the Department of Chemistry, University of California, Berkeley, Calif.

Thin layer chromatography (TLC) was carried out on precoated silica gel 60F-254 (E. Merck) or reverse-phase (RP-18, F-254, E. merck, or MKC$_{18}$F, Whatman) plates. For column chromatography, silica gel 60 (230-400 mesh, E. Merck) was used. All manipulations of compounds sensitive to near ultraviolet light were performed under an orange safety lamp.

COMPOUND 3d

3-Acetoxy-4-Nitrobenzoic Acid

3-Hydroxy-4-nitrobenzoic acid (Aldrich, 95%; 4.82 g; 25 mmol) was suspended in pyridine (2 mL) and acetic anhydride (20 mL) and heated at 100° C. for 30 min. After cooling, the mixture was evaporated to near dryness to give a yellow solid which was suspended in water (40 mL). The solid dissolved slowly and temperature rose to 50°-60° C. to give a clear solution, which on cooling yield the product, Compound 3d. The crystalline yellow solid was collected by filtration, washed with water, and dried. Yield 3.72 g. M.p. 182°-184° C. The mother liquor, on acidification to pH 1 with concentrated hydrochloric acid, gave a further crop (1.58 g) of slightly impure Compound 3d, as shown by thin layer chromatography (silica: butanol:acetic acid:water; 4:1:1 v/v). Yield, 94%.

$^1$H NMR (CDCl$_3$, CD$_3$OD) δ2.36(s 3H, CH$_3$), 4.50 (s,—OH), 7.90 (s, 1H, H-2), 8.08 (2s, 2H, H-5,6).

Anal: Calculated for C$_9$H$_7$NO$_6$: C, 48.01; H, 3.13; N, 6.22.

Found: C, 48.13; H, 3.22; N, 6.12.

COMPOUND 3e

Tert-Butyl 3-Hydroxy-4-Nitrobenzoate

Compound 3d (2.0 g, 8.9 mmol) was heated at reflux with thionyl chloride (6 mL) and dimethylformamide (1 drop) until all the solid had dissolved (10 min), and there was no further gas evolution (5 min). The solution was cooled, evaporated to dryness to yield a yellow solid which was treated with dry tert-butanol (3mL, 32 mmol), dry pyridine (4 mL, 49 mmol) in chloroform (5 mL) at 0° C. under an argon atmosphere. After the addition, the mixture was refluxed overnight, cooled and evaporated to dryness, and then dissolved in hot methanol (30 mL). Concentrated aqueous potassium hydroxide (45% w/v) was added dropwise with stirring until a constant pH of about 11 was maintained for 30 min, adding portions of water as necessary to dissolve the K$^+$ salt. The excess alkali was neutralized with a few drops of glacial acetic acid, and the methanol was removed by rotary evaporation to leave an orange solid which was dissolved in water (30 mL). After filtration, the product Compound 3e was precipitated by acidification to pH 5 with concentrated hydrochloric acid. Yield, after washing and desiccation, of a pale yellow powder, was 0.80 g (38%) which could be recrystallized from ethanol. M.p. 117°-119° C.

$^1$H NMR δ1.60 (s, 9H, C(CH$_3$)$_3$), 7.50 (dd, 1H, J=2.5, 9 Hz, H-6) 7.80 (d, 1H, J=2.5 Hz, H-2), 8.08 (d, 1H, J=9 Hz, H-5).

Anal. Calculated for C$_{11}$H$_{13}$NO$_5$: C, 55.23; H, 5.48; N, 5.86.

Found: C, 55.24; H, 5.34; N, 5.79.

When the aqueous filtrate was acidified to pH 2, 3-hydroxy-4-nitrobenzoic acid, 0.89 g. of product was recovered (55%).

COMPOUND 3f

1-(5-Tert-Butoxycarbonyl-2-Nitrophenoxy)-2-(5-Methyl-2-Nitrophenoxy)Ethane

A mixture of Compound 3e (239 mg, 1 mmol), 1-bromo-2-(5-methyl-2-nitrophenoxy)ethane, see G. Grynkiewicz, et al. (1985), (286 mg, 1.1 mmol), K$_2$CO$_3$ (83 mg, 0.6 mmol) in dry N-methylpyrrolidinone (0.75 mL) was heated at 140° C. for 10 min with protection from moisture, cooled and H$_2$O added dropwise to precipitate the product, Compound 3f. After filtration, recrystallization from EtOH gave a white solid, m.p. 113°-114° C. Yield, 383 mg (92%).

$^1$H NMR δ 1.60 (s, 9H, C(CH$_3$)$_3$), 2.38 (s, 3H, Ar-CH$_3$), 4.48 (s, 4H, —CH$_2$CH$_2$—), 6.7-6.9, 7.6-7.7 (2m, 6H, aromatic).

Anal. Calculated for C$_{20}$H$_{22}$N$_2$O$_8$ C, 57.41; H, 5.30; N, 6.70. Found: C, 57.59; H, 5.27; N, 6.71.

COMPOUND 3g

1-(2-Amino-5-Tert-Butoxycarbonylphenoxy)-2-(2-Amino-5-Methylphenoxy)Ethane

Compound 3f (264 mg, 0.63 mmol) was catalytically hydrogenated at room temperature and pressure with 50 mg of 5% Pd/C in ethyl acetate ethanol (1:1). Uptake was complete within 1 hr; the reaction mixture was filtered and evaporated to dryness to yield the product, compound 3 g. Recrystallization from ethanol gave shining colorless plates, m.p. 154°-156° C. Yield 184 mg (81%).

$^1$H-NMR δ 1.60 (s, 9H, C(CH$_3$)$_3$), 2.20 (s, 3H, ArCH$_3$), 4.37 (s, 4H, CH$_2$CH$_2$), 6.53-6.8, 7.4-7.6 (2m, 6H, aromatic).

Anal. Calculated for C$_{20}$H$_{26}$N$_2$O$_4$ C, 67.01; H, 7.31; N, 7.82. Found: C, 67.01; H, 7.34; N, 7.92.

COMPOUND 3h

1-[2-[Bis[(Methoxycarbonyl)Methyl]Amino]-5-Tert-Butoxycarbonylphenoxy]-2-[2-[Bis(Methoxycarbonyl)-Methyl]Amino]-5-Methylphenoxy]Ethane A mixture of Compound 3g (143 mg, 0.4 mmol), 1,8-bis(dimethylamino)naphthalene (Proton Sponge) (0.69 g, 0.32 mmol), and methyl bromoacetate (0.3 mL, 0.32 mmol) was heated at 125° C. overnight under N$_2$. An additional 0.16 mmol each of Proton Sponge and methyl bromoacetate were added and heating continued for 48 hr. The reaction mixture was diluted with toluene (20 mL), filtered, and washed with 1M phosphate buffer, pH 2 (3×5 mL) and water (1×5 mL). After drying over sodium sulfate, and evaporation to dryness, trituration with ethanol yielded the product, Compound 3h. Recrystallization from ethanol gave 203 mg of white solid (78%). M.p. 98°-101° C.

$^1$H NMR δ 1.58 (s, 9H C(CH$_3$)$_3$), 2.23 (s, 3H, ArCH$_3$), 3.53 (s, 12H, OCH$_3$), 4.09, 4.17, 4.26 (3s, 12H CH$_2$) 6.6-6.8, 7.4-7.5 (2m 6H, aromatic).

Anal. Calculated for $C_{32}H_{42}N_2O_{12}$: C, 59.43; H, 6.55; N, 4.33. Found: C, 59.07; H, 6.42; N, 4.36.

COMPOUND 3j

Diazo-2-Tetramethyl Ester

1-[2-[Bis[(Methoxycarbonyl)Methyl]Amino]-5-(Diazoacetyl)Phenoxy]-2-[2-[Bis(Methoxycarbonyl)-Methyl]Amino]-5-Methylphenoxy]Ethane Compound 3h (100 mg, 0.15 mmol), was dissolved in 20% trifluoroacetic acid/methylene chloride (v/v, 2.5 mL) and kept at room temperature overnight. After dilution with chloroform (10 mL), the reaction mixture was washed with saturated sodium bicarbonate solution, dried over sodium sulfate and evaporated to dryness to yield the benzoic acid derivative as a colorless foam. The crude acid was dissolved in methylene chloride (2 mL) and oxalyl chloride (100 μl, 1.1 mmol) and refluxed gently for 10 min before being evaporated to dryness to give the crude acid chloride. This was dissolved in methylene chloride (about 0.5 mL) and an excess of ethereal alcohol-free diazomethane solution (about 10 mmol, prepared from Diazald in 2-ethoxyethanol), added while cooling to 0° C. After keeping overnight at room temperature, the reaction mixture was evaporated to dryness to yield the crude product, Compound 3j, as a part-crystalline solid which was purified by silica gel chromatography eluting with ethyl acetate/hexane. The resulting yellow oil crystallized on trituration with ethanol and was recrystallized from ethanol to give Compound 3j as lemon-colored crystals. M.p. 105° C. Yield, 42.3 mg (46%).

$^1$H NMR δ 2.23 (s, 3H, ArCH$_3$), 4.10, 4.20, 4.27 (3s, 12H, CH$_2$), 5.80 (s, 1H, CHN$_2$) 6.6–6.8, 7.1–7.4 (2m, 6H, aromatic).

Anal. Calculated for $C_{29}H_{34}N_4O_{11}$: C, 56.67; H, 5.58; N, 9.12. Found: C, 56.39; H, 5.51; N, 9.26.

COMPOUND 4b

3-Methoxy-4-Nitrobenzoic Acid

3-Hydroxy-4-nitrobenzoic acid (Aldrich, 95%) 1.93 g, 10 mmol), K$_2$CO$_3$ (4 g) and methyl sulphate (3.8 mL, 40 mmol) suspended in dry N-methyl pyrrolidinone (10 mL), were heated at 100° C. for 1 hr under an nitrogen atmosphere. After cooling, addition of water precipitated the methyl ester which was filtered, dissolved in hot methanol and saponified by adding 1M sodium hydroxide solution (11 mmol). After 30 min, the reaction mixture was evaporated to dryness, dissolved in water and acidified to pH 2 with concentrated hydrochloric acid to yield the product, Compound 4b, which was filtered and dessicated. Yield, 1.88 (95%).

COMPOUND 4c

Tert-Butyl 3-Methoxy-4-Nitrobenzoate

Compound 4b (0.79 g, 4 mmol) was refluxed in thionyl chloride (5 mL) for 1 hr, cooled and evaporated to dryness. A solution of dry pyridine (0.81 mL, 10 mmol), dry tert-butanol (0.95 mL), 10 mmol in chloroform (2 mL) was added and the reaction mixture was refluxed 2 hr, with protection for moisture. After keeping overnight at room temperature, the mixture was evaporated to dryness, dissolved in chloroform (30 mL), washed with dilute hydrochloric acid 3 × 15 mL), derived over sodium sulfate and evaporated to dryness to yield the crude product, Compound 4c, as a yellow solid. Yield 0.54 g (53%). $^1$H NMR δ 1.60 s, 9H, C(CH$_3$)$_3$), 3.97 (s, 3H, OCH$_3$), 7.5–7.8 (m, 3H, aromatic).

COMPOUND 4d

Tert-Butyl 4-Amino-3-Methoxybenzoate

The crude nitrobenzoate Compound 4c (0.5 g, about 2 mmol) was catalytically hydrogenated at room temperature and pressure with 50 mg of 5% Pd/C in ethyl acetate: 95% aqueous ethanol (1:1). Hydrogen uptake was complete after 5 hr. After keeping overnight, the reaction mixture was filtered and evaporated to dryness to yield the product, Compound 4d, as a colorless oil which crystallized on trituration with MeOH. Recrystallization of 95% aqueous ethanol afforded 295 mg (65%) white crystals.

Anal. Calculated for $C_{12}H_{17}NO_3$: C, 64.55, H, 7.68; N, 6.27. Found: C, 64.46; H, 7.68; N, 6.23.

COMPOUND 4e

Tert-Butyl 4-Bis[(Methoxycarbonyl)Methyl]Amino-3-Methoxybenzoate

A mixture of compound 4d (226 mg, 1 mmol), 1,8-bis(dimethylamino)naphthalene (0.86 g, 4 mmol) and methyl bromoacetate 0.38 mL, 4 mmol) were heated at 125° C. under argon for 96 hr, with a further addition of 2 mmol each of 1,8-bis(dimethylamino)naphthalene and methyl bromoacetate after 24 hr. After cooling, the reaction mixture was diluted was ethyl acetate-toluene (1:1, 30 mL), filtered, and washed with 1M phosphate buffer pH 2 (3×10 mL) and then water (1×10 mL). The organic layer was dried using sodium sulfate and evaporated to dryness to yield an oil, which was chromatographed on silica gel with ethyl acetate-hexane as eluent to yield Compound 4e as a colorless oil (175 mg, 47%). $^1$H NMR δ 1.53 (s, 9H, C(CH$_3$)$_3$), 3.73 (s, 6H, CO$_2$CH$_3$), 3.80 (s, 3H, ArOCH$_3$), 4.15 (s, 4H, CH$_2$), 6.68 (d, 1H, J=8 Hz, H-5), 7.43 (s, 1H, H-2), 7.48 (d, 1H,J=8 Hz, H-6).

COMPOUND 4f

Tert-Butyl 4-Bis[(Methoxycarbonyl)Methyl]Amino-2'-Diazo-3-Methoxyacetophenone The free acid of Compound 4e was prepared by dissolving the ester Compound 4e (90 mg, 0.24 mmol) in 20% trifluoroacetic acid/methylene chloride (2.5 mL, v/v) and keeping at room temperature overnight. The reaction mixture was diluted with methylene chloride, extracted into saturated aqueous sodium bicarbonate (1×15 mL), acidified with glacial acetic acid and re-extracted (6×10 mL) with chloroform. After drying of the organic layer sodium sulfate, evaporation of the solvent yield the free acid as a white solid, yield 66 mg (87%). The crude product was dissolved in methylene chloride (3 mL), and oxalyl chloride (100 μL, 1.1 mmol) added dropwise and refluxed gently for 10 min. The crude acid chloride, after evaporation of the reaction mixture, was redissolved in chloroform (2 mL) and added to an excess of ethereal alcohol-free diazomethane solution (about 10 mmol) at 0° C. The solution was allowed to warm up to room temperature over 2 h and then kept overnight. Evaporation of the solvent yielded the crude product which was separated by silica gel chromatography with ethyl acetate-hexane. Yield of pale yellow oil, 64 mg (80%).

$^1$H NMR 3.73 (s, 6H, CO$_2$CH$_3$), 3.80 (s, 3H, ArOCH$_3$), 4.15 (s, 4H, CH$_2$) 5.78 (s, 1H, CHN$_2$), 6.62 (d, 1H, J=8 Hz, H-5), 7.10 (dd, 1H, J=2, 8 Hz, H-6), 7.33 (d, 1H, J=2 Hz, H-2).

COMPOUND 5b 1,2-Bis(5-Tert-Butoxycarbonyl-2-Nitrophenoxy)Ethane

A mixture of Compound 3e (0.24 g, 1 mmol) and potassium carbonate (0.14 g, 1 mmol) in N-methyl pyrrolidone (1 mL) were heated at 125° C. under argon. After all gas evolution had ceased (5 min), 1,2-dibromoethane equal portions (total 102 μL, 1.2 mmol) was added in three at 5, 20, and 35 min. The mixture was then heated for 15 min, cooled and water added dropwise to precipitate the crude product as a white solid, which was collected by filtration and washed thoroughly with water. Recrystallization from ethanol afforded Compound 5b as brown crystals (0.21 g, 83%). M.p. 155°-157° C.

$^1$H NMR δ 1.60 (s, 18H, C(CH$_3$)$_3$), 0.53 (s, 4H, CH$_2$), 7.5-7.8 (m, 6H, aromatic).

Anal. Calculated for C$_{24}$H$_{28}$N$_2$O$_{10}$:C, 57.14; H, 5.59; N, 5.55. Found: C, 56.81; H, 5.50; N, 5.78.

COMPOUND 5c 1,2-Bis(2-Amino-5-Tert-Butoxycarbonylphenoxy)Ethane

Compound 5b (0.42 g, 0.83 mmol) was dissolved in ethyl acetate:ethanol (45 mL, 2:1) and catalytically hydrogenated at room temperature and pressure with 100 mg 5% Pd/C. Hydrogen uptake was complete within 1 hr. The reaction mixture was filtered and evaporated to dryness to yield the product, Compound 5c. Recrystallization from ethanol gave a white powder (2 crops, total 0.35 g, 95%). M.p. 138° C.

$^1$H NMR δ 1.58 (s, 18H,C(CH$_3$)$_3$), 4.20 (s, br, 4H, NH$_2$), 4.40 (s, 4H, CH$_2$), 6.60(d, 2H, H-3), 7.45 (m, 4H, H-4,6).

Anal. Calculated for C$_{24}$H$_{32}$N$_2$O$_6$:C, 64.84; H, 7.26; N, 6.30. Found: C, 64.61; H, 7.33; N, 6.74.

COMPOUND 5d 1,2-Bis[2-Bis(Methoxycarbonylmethyl)]Amino-5-Tert Butoxycarbonylphenoxy]Ethane A mixture of Compound 5c (185 mg., 0.42 mmol), 1,8-bis(di-methylamino)naphthalene (0.86 mg, 4 mmol), and methyl bromoacetate (0.38 mL, 4 mmol) were heated for 5 days at 125° C. under Ar. The resulting solid was dissolved with ethyl acetate-chloroform (20 mL), filtered, and washed with 1M phosphate buffer, pH 2 (1×5 mL) and H$_2$O (1×5 mL). After drying over sodium sulfate, and evaporation to dryness, the resulting solid was recrystallized from ethanol to give the product Compound 5d, as a white solid (0.23 g, 64%). M.p. 144°-145° C. $^1$H NMR δ 1.54 (s, 18H C(CH$_3$)$_3$), 3.57 (s, 12H, OCH$_3$), 4.17 (s, 8H, NCH$_2$), 4.28 (s, 4H, OCH$_2$), 6.69 (d, 2H, J=9 Hz, H-3), 7.48 (s, 2H, H-6), 7.52 (d, 2H, J=9 Hz, H-4).

Anal. Calculated for C$_{36}$H$_{48}$N$_2$O$_{14}$:C, 59.00; H, 6.60; N, 3.82. Found: C, 58.77; H, 6.46; N, 3.80.

COMPOUND 5e 1,2-Bis[2-[Bis(Methoxycarbonylmethyl)]Amino-5-(Diazoacetyl)Phenoxy]Ethane Compound 5d (100 mg, 0.11 mmol) was dissolved in 20% trifluoroacetic acid/methylene chloride (v/v, 2.5 mL), kept at ambient temperature overnight and then evaporated to dryness. The resulting white solid was suspended in methylene chloride (2 mL) containing 1 drop of dry dimethylformamide, oxalyl chloride (0.5 mL, 5.7 mmol) was added and the mixture refluxed for 15 min. The resulting yellow solution was evaporated to dryness, redissolved in methylene chloride (2 mL) and treated with an excess of ethereal, alcohol-free diazomethane at 0° C. After standing overnight at room temperature, the solution was evaporated to dryness and the product, 5e, was separated by silica gel chromatography with ethyl acetate-hexane as eluent. Recrystallization from ethanol gave a pale yellow solid (31 mg., 42%). M.p. 151° C. (decomp.).

$^1$H NMR δ 3 58 (s, 12H, OCH$_3$), 4.18 (s, 8H, NCH$_2$), 4.28 (s, 4H, OCH$_2$) 5 81 (s, 2H, CHN$_2$), 6.78 (d, 2H, J=9 Hz, H-3), 7.20 (dd, 2H, J=2.5, 9 Hz, H-4), 7.42 (d, 2H, J=2.5 Hz, H-6).

Anal. Calculated for C$_{30}$H$_{32}$N$_6$O$_{12}$:C, 53.89; H, 4.82; N, 12.57. Found: C, 53.89; H, 4.92; N, 12.39.

EXAMPLE 1

Saponification of Esters

Diazo-2 tetramethyl ester, Compound 3J, was saponified to the tetra-anion by dissolution in methanol (gentle heat), addition of an excess of aqueous 1M potassium hydroxide solution and keeping at room temperature several hours, preferably overnight. Diazo-2 is stable under such conditions of dilute aqueous base but on concentration to a solid decomposes and becomes light-insensitive. The purity of diazo-2 solutions can be determined by measuring the extent of absorbance change on complete photolysis (FIG. 1B) as contaminants contribute absorbance at 355 nm. Diazo-1, -3, and -4 esters were saponified analogously.

EXAMPLE 2

Preparation of Acetoxymethyl (AM) Esters

Diazo-2 tetramethyl ester, Compound 3j, (2.0 mg) was dissolved in methanol (100 L) and saponified by the addition of tetramethylammonium hydroxide (40 μL, 1M aqueous solution). After keeping at room temperature overnight, glacial acetic acid (2.3 μL, 40 μmol) was added and the solution evaporated to dryness (waterbath <30° C.) and desiccated. The residue was suspended in methylene chloride (0.5 mL,) then diisopropylethylamine (5 μL) and acetoxymethyl bromide (10 μL) were added with stirring. After 6 h, an additional 10 μL each of amine and bromide were added and the mixture stirred overnight at room temperature. The reaction mixture was diluted with chloroform (1 mL) and extracted with 50 mM phosphate buffer, pH 6.8 (1×1 mL), dried over sodium sulfate, evaporated to dryness and separated by silica gel chromatography, eluting with ethylacetate-hexane to afford diazo-2 AM as a colorless gum. Stock solutions were prepared in dimethylsulfoxide and stored frozen. Diazo-3 and -4 AM esters were prepared similarly.

EXAMPLE 3

Calcium and Magnesium Affinities

Ca$^{2+}$-binding constants for chelators before and after photolysis were determined by monitoring UV spectra during titration of EGTA or HEEDTA buffers to varying free Ca$^{2+}$ levels.

Either the ratio of, for example, [Ca.EGTA] to free [EGTA] was adjusted at a constant pH, or the pH was varied while [Ca.EGTA]=[EGTA]. These two approaches gave equivalent answers for pH>7 whenever directly tested, because of the pH insensitivity of BAPTA-like ligands (see FIG. 1 legend for more details). The apparent dissociation constants of Ca.EGTA and Ca.HEEDTA were calculated as described by R. Y. Tsien (1980); see also R. Y. Tsien, et al. (1986), S. R. Adams, et al. (1980), Grynkiewicz, et al., (1985), and Jackson, et al. (1987).

Free [$Mg^{2+}$] was likewise controlled by Mg/EGTA buffers, assuming an apparent dissociation constant for the Mg.EGTA complex (including its monoprotonated form) of 6 mM at pH 7.60 in 0.1M ionic strength; see R. Y. Tsien, et al. (1986) and A. E. Martell, et al. (1974).

EXAMPLE 4

Quantum Efficiencies of Photolysis

The photolysis quantum efficiencies of diazo chelators were determined by alternately irradiating a buffered solution of the substrate with a known intensity of longwave UV light, and measuring the absorbance spectrum, in apparatus described by S. R. Adams, et al. (1988), supra.

EXAMPLE 5

Flash Photolysis

Kinetics of the conversion of diazo-2 and diazo-3 to the carboxylic acid products and the kinetics of $Ca^{2+}$-binding by photolyzed diazo-2 were measured by flash photolysis and pH monitoring. The experiments were done in a Dialog apparatus (Garching, FRG) normally used for temperature jumps. The xenon flash lamp was a Model 6100SP7 (Photochemical Research Associates, London, Ontario, Canada) modified to give a light pulse with a full width at half maximum of 85 $\mu$s. The output of the xenon lamp was passed through a UG-2 filter to yield broad-band UV radiation in the 330-390 range. Since neither the flash lamp nor the kinetic spectrometer was optimized for light energy, the response amplitudes achieved in the experiments are far from those attainable during a biological experiment.

The cresol red used for report pH changes in the sample solutions was probed with 572 nm light from a 200 W Hg-Xe arc lamp and a grating monochromator. Glass filters blocking wave-lengths shorter than 455 nm and 530 nm were placed in front of the reference and signal photomultipliers respectively to minimize stray light from the photolytic flash from entering the detector. Despite these precautions, some flash artifact still occurred, as evidenced by the initial spikes in the records shown in FIG. 2. The transmitted 572 nm light signal was digitized by a Biomation 805 (Biomation, Cupertino, Calif.) transient waveform recorder triggered by a sync pulse generated by the xenon flash lamp power supply. The digitized data were transferred via a PET microcomputer (Commodore Business Machines, Santa Clara, Calif.) to VAX 11/785 minicomputer where all data reduction and analyses were performed. The program DISCRETE was used to analyze the data for multiple exponential decay times.

Experiments to determine the rate of photochemical product formation from diazo-2 were made at low free $Ca^{2+}$ (either no added $Ca^{2+}$ or in the presence of 40 $\mu$M BAPTA) and high free $Ca^{2+}$ (1 mM $CaCl_2$) $Ca^{2+}$-binding kinetics of the photolyzed diazo-2 was studied using samples which contained 70 $\mu$M diazo-2, 2.0 mM $K_2H.HEEDTA$, and 1.0 mM $CaCl_2$. For the diazo-3 experiments, the samples contained either 35 $\mu$M or 70 $\mu$M diazo-3. All solutions contained 100 mM KCl as background electrolyte and enough cresol red to yield a maximum absorbance of 0.07 in the sample cell. The measurements were made at 20° C. and pH 8.0, adjusted with KOH under in the sample cell.

Control flashes delivered to solutions containing cresol red but from which diazo compound was omitted (FIG. 2A, dotted trace) showed that flash duration and detector recovery did not limit time resolution.

EXAMPLE 6

In Vivo Biological Tests

For preliminary biological tests, Fisher rat embryo fibroblast of the REF52 cell line were cultured as described by J. P. Y. Kao, et al. (1989).

For testing diazo-2, REF52 cells were incubated for 30 min at 25° C. in Dulbecco's modified Eagle's medium, buffered at pH 7.4 with 20 mM HEPES and containing 1 $\mu$M diazo-2/AM and 10 $\mu$M fluo-3/AM. For control experiments using diazo-3, the cells were incubated for 90 min at 25° C. in DMEM, buffered to pH 7.4 with 20 mM HEPES and containing 1 $\mu$M diazo-3/AM and 10M fluo-3/AM. After loading, the cells were gently washed, transferred into Hanks' Balanced Salt Solution containing 0.2 mM sulfinpyrazone to inhibit non-specific organic anion transport (see Tsien, 1989), and mounted on a 25° C. microscope stage for experimentation.

FLASH PHOTOLYSIS

Flash photolysis of trapped cellular diazo-2 and the concomitant monitoring of intracellular free $Ca^{2+}$ concentration with fluo-3, a fluorescent $Ca^{2+}$ indicator, were performed using methodology and instrumentation described in A. Minta, et al (1989) and J. P. Y. Kao, et al. (1989). Briefly, output form a Xe arc lamp was passed through a monochromator to yield the 490 nm light used to probe the fluo-3 trapped intracellularly. The fluo-3 fluorescence images of cells were recorded using a SIT TV camera. Images were stored on a high-resolution monochrome laser disc recorder (Panasonic TQ-2028) for delayed processing. Photolyses were performed by briefly moving a chopper mirror to send broad-band UV from an XBO 75 W xenon arc lamp and UG-2 filter into the microscope instead of 490 nm fluo-3 excitation. The microscope objective (Nikon UV-CF, 40X) was chosen for its high UV transmission and numerical aperture (1.3). A custom dichroic mirror (DR505LP, Omega Optical, Inc., Brattleboro, Vt.) was placed in the microscope epifluorescence filter cube to reflect both UV and 490 nm light efficiently while retaining high transmission at wavelengths >510 nm, where fluo-3 emits strongly. Data acquisition by the SIT camera and the flash photolysis were under the coordinated control of a Micro-PDP-1183 computer. The same computer was used to analyze the fluorescence images acquired during the experiment.

EXAMPLE 7

Covalent Modification of Lysine by Photochemical Intermediates

To study the extent to which biological substrates are covalently modified by reactive intermediates generated by the photolysis of the diazoketones, 100 $\mu$M diazo-3 in the presence of 10 mM phosphate and either 100 mM KCl or 100 mM lysine.HCl, at pH 7.2 was photolyzed. The photolysates were analyzed by HPLC (Waters Associates, Inc., Milford, Mass.; C-18 column, Supelco, Inc., Bellefonte, Pa.), with 10 mM $KH_2PO_4/K_2HPO_4$ buffer at pH 7.2 as eluting solvent. The absorbance of the eluate at 254 nm was monitored. Before being injected onto the column, concentrated stock solutions of either KCl or lysine.HCl were added to the photolysate to insure that the electrolyte composition of the injected samples were identical. Thus, 10 µL of 1M KCl were added to 100 µL of the samples of diazo-3 photolyzed in lysine.HCl, while 10 µL of 1M lysine.HCl were added to 100 µL of the sample of diazo-3 photolyzed in KCl.

This new class of chelators disclosed herein extend the ability to control the concentration of $Ca^{2+}$ inside cells. They are extremely useful to biological researchers trying to study the many cellular functions which calcium ion is now believed to control. Such biological functions include, for example, ion-gating and muscle contractions.

While only a few embodiments of the present invention have been shown and described herein, it will become apparent to those skilled in the art that various modifications and changes can be made in these chelators whose affinity is for calcium ion is increased by illumination without departing from the spirit and scope of the present invention. All such modifications and changes coming within the scope of the appended claims are intended t be carried thereby.

We claim:

1. A compound of the formula:

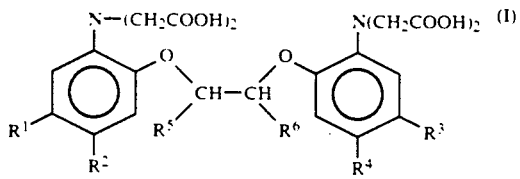

and the salts or the non-polymeric esters thereof wherein $R^1$ and $R^3$ are each independently selected from —H, —OH, —$CH_3$, —F, —Cl, —Br, —I, —COOH, —CN, —$NO_2$ or —$NHR^7$ wherein $R^7$, is independently selected from —H, methyl, or ethyl;

$R^2$ is —(C=O)$CR^8$=N=N, wherein $R^8$ is independently selected from —H, C1-C4 alkyl, phenyl, —COOH, —$COOR^7$, —(C=O)$CH_3$, or —$CF_3$, wherein $R^7$ is defined herinabove;

$R^4$ is independently selected from $R^2$, —H, —$CH_3$, —$CH_2CH_3$, —F, —Cl—, —Br, —I, —COOH, —CN or —$NO_2$;

$R^5$ and $R^6$ are each independently selected from —H, —$CH_3$, —$C_2H_5$, phenyl, or —$CH_2OH$, or $R^5$ and $R^6$ together form —$(CH_2)_m$—Y—$(CH_2)_n$— where m and n are each independently 1 or 2, and Y is selected from —$CH_2$—, —O—, —$NHR^7$, —S— or —S—S—, wherein $R^7$ is defined herein above.

2. The compound of claim 1 wherein $R^8$ is hydrogen.

3. The compound of claim 2 wherein $R^4$ is selected from —H, $CH_3$ or $R^2$.

4. The compound of claim 3 wherein $R^4$ is —$CH_3$.

5. The compound of claim 4 wherein $R^1$ and $R^3$ are each —H.

6. The compound of claim 5 wherein $R^5$ and $R^6$ are each —H.

7. A method for use for a compound of the formula:

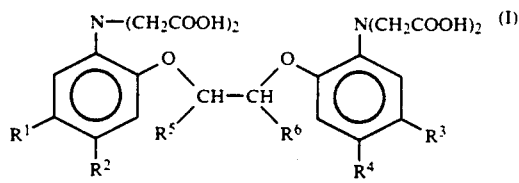

and the salts or the non-polymeric esters thereof wherein $R^1$ and $R^3$ are each independently selected from —H, —OH, —$CH_3$, —F, —Cl, —Br, —I, —COOH, —CN, —$NO_2$ or —$NHR^7$ wherein $R^7$, is independently selected from —H, methyl, or ethyl;

$R^2$ is —(C=O)$CR^8$=N=N, wherein $R^8$ is independently selected from —H, C1-C4 alkyl, phenyl, —COOH, —$COOR^7$, —(C=O)$CH_3$, or —$CF_3$, wherein $R^7$ is defined hereinabove;

$R^4$ is independently selected from $R^2$, —H, —$CH_3$, —$CH_2CH_3$, —F, Cl, —Br, —I, —COOH, —CN or —$NO_2$;

$R^5$ and $R^6$ are each independently selected from —H, —$CH_3$, —$C_2H_5$, phenyl, or —$CH_2OH$, or $R^5$ and $R^6$ together form —$(CH_2)_m$—Y—$(CH_2)_n$— where m and n are each independently 1 or 2, and Y is selected from —$CH_2$—, —O—, —$NHR^7$, —S— or —S—S—, wherein $R^7$ is defined herein above for the chelation of calcium ion in aqueous solution, which method comprises:

(a) contacting an aqueous sample containing calcium ion with an effective quantity of the compound of structure (I);

(b) irradiating the aqueous solution obtained with electromagnetic radiation effective to convert the diazo moiety and obtain the active calcium ion chelating agent.

8. The method of use of claim 7 wherein in step (a) the effective amount of the compound of structure (I) is a molar ratio between about 0.5 and 10 times the $Ca^+$ ion concentration.

9. The method of use of claim 7 wherein:
in step (b) the electromagnetic radiation is ultraviolet light between about 300 and 450 nm.

10. The method of use of claim 7 wherein in the compound of structure (I), $R^8$ is hydrogen.

11. The method of use of claim 10 wherein $R^4$ is —$CH_3$.

12. The method of use of claim 11 wherein $R^1$, $R^3$, $R^5$ and $R^6$ are each —H.

* * * * *